US 12,257,038 B2

(12) United States Patent
Otsuka et al.

(10) Patent No.: US 12,257,038 B2
(45) Date of Patent: Mar. 25, 2025

(54) ELECTRONIC DEVICE, CONTROL METHOD FOR THE ELECTRONIC DEVICE, AND STORAGE MEDIUM

(71) Applicant: CASIO COMPUTER CO., LTD., Tokyo (JP)

(72) Inventors: Toshihiko Otsuka, Tokyo (JP); Takahiro Tomida, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 218 days.

(21) Appl. No.: 17/202,508

(22) Filed: Mar. 16, 2021

(65) Prior Publication Data

US 2021/0298620 A1   Sep. 30, 2021

(30) Foreign Application Priority Data

Mar. 24, 2020   (JP) ................. 2020-052655

(51) Int. Cl.
*A61B 5/024*   (2006.01)
*A61B 5/00*   (2006.01)
(Continued)

(52) U.S. Cl.
CPC ........ *A61B 5/02416* (2013.01); *A61B 5/0285* (2013.01); *A61B 5/7246* (2013.01);
(Continued)

(58) Field of Classification Search
CPC . A61B 5/02416; A61B 5/0285; A61B 5/7246; A61B 5/7275; A61B 5/7278; A61B 5/0077; G16H 40/67; G16H 50/30
See application file for complete search history.

(56) References Cited

U.S. PATENT DOCUMENTS

2016/0338599 A1\* 11/2016 DeBusschere ....... A61B 5/7246
2018/0042486 A1\* 2/2018 Yoshizawa ......... A61B 5/02125
(Continued)

FOREIGN PATENT DOCUMENTS

JP   2008113876 A   \*   5/2008
JP   2016190022 A         11/2016
(Continued)

OTHER PUBLICATIONS

WO2018066679A1 (Kyocera Korp). Translated by Espacenet. Apr. 12, 2018 [retrieved Feb. 6, 2024] (Year: 2018).\*
(Continued)

*Primary Examiner* — Colin T. Sakamoto
*Assistant Examiner* — Andrew W Begeman
(74) *Attorney, Agent, or Firm* — Holtz, Holtz & Volek PC

(57) ABSTRACT

An electronic device includes a processor that acquires first pulse wave amplitude information and second pulse wave amplitude information each indicating an amplitude of a pulse wave of a body, based on video information of respective first and second videos of the body obtained by image-capturing at least a portion of the body, with the second video being obtained after the first video. The processor compares the first pulse wave amplitude information with the second pulse wave amplitude information to output a comparison result indicating a degree of variation in a blood flow of the body, and stores the outputted comparison result in a memory, and acquires a trend in variation of the blood flow of the body based on a most recently acquired comparison result and the comparison result previously stored in the memory.

9 Claims, 24 Drawing Sheets

(51) Int. Cl.
*A61B 5/0285* (2006.01)
*G16H 20/30* (2018.01)
*G16H 40/67* (2018.01)
*G16H 50/30* (2018.01)

(52) U.S. Cl.
CPC .......... *A61B 5/7275* (2013.01); *A61B 5/7278* (2013.01); *A61B 5/7445* (2013.01); *G16H 20/30* (2018.01); *G16H 40/67* (2018.01); *G16H 50/30* (2018.01); *A61B 5/0077* (2013.01)

(56) References Cited

U.S. PATENT DOCUMENTS

2019/0083353 A1* 3/2019 Khurana .............. A61H 9/0092
2021/0068689 A1* 3/2021 Ochs .................... A61B 5/1118

FOREIGN PATENT DOCUMENTS

JP           2019025071 A      2/2019
WO    WO-2018066679 A1 *   4/2018

OTHER PUBLICATIONS

JP2008113876A (Kao Corp). Translated by Espacenet. May 22, 2008 [retrieved Feb. 6, 2024] (Year: 2008).*
Japanese Office Action dated May 24, 2022 (and English translation thereof) issued in counterpart JP Application No. 2020-052655.

* cited by examiner

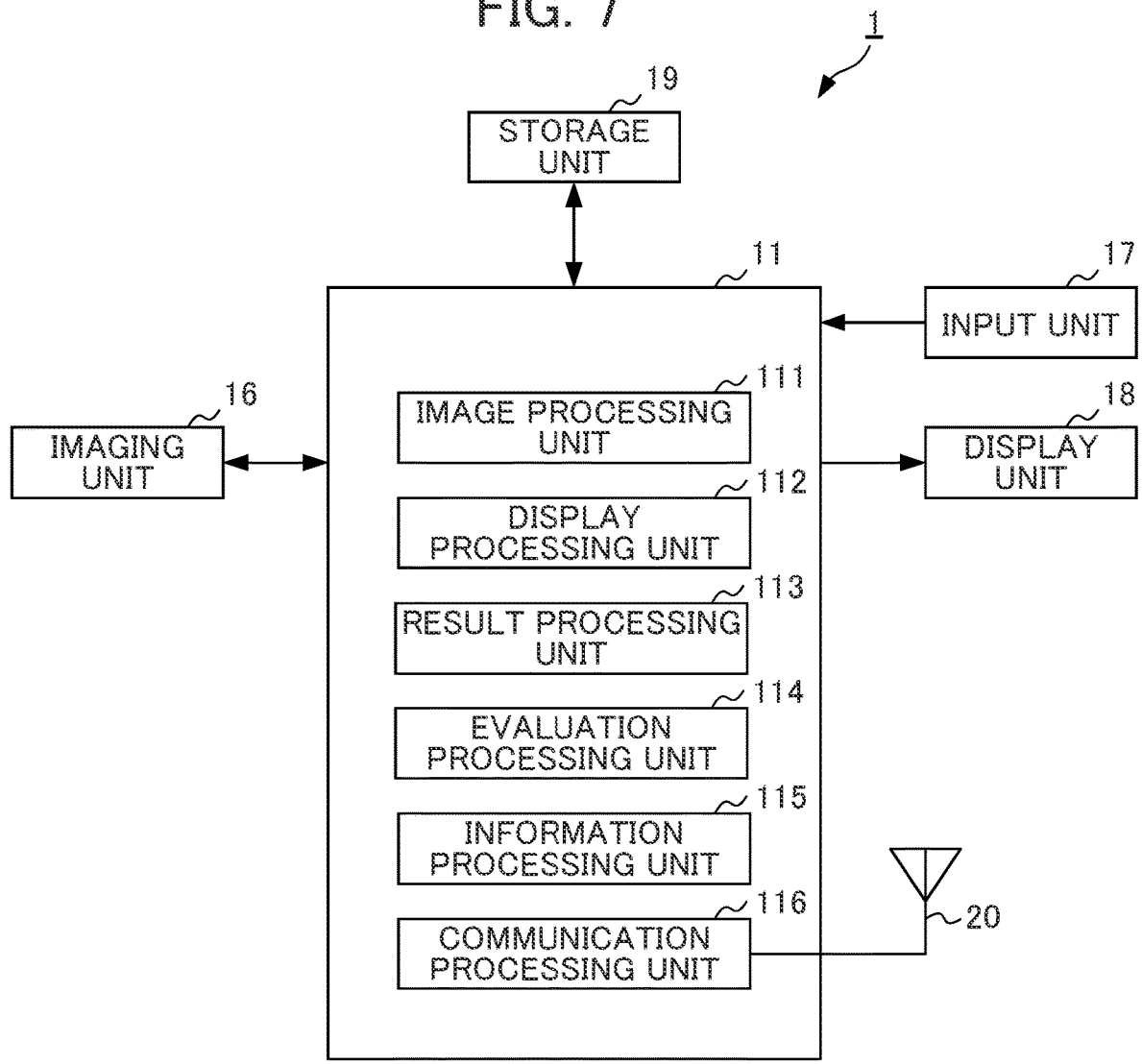

RGB LAMINATION VALUE

RGB LAMINATION VALUE

RGB LAMINATION VALUE

RGB LAMINATION VALUE

G LUMINANCE VALUE

G LUMINANCE VALUE

G LUMINANCE VALUE

G LUMINANCE VALUE

G-R VALUE

G-R VALUE

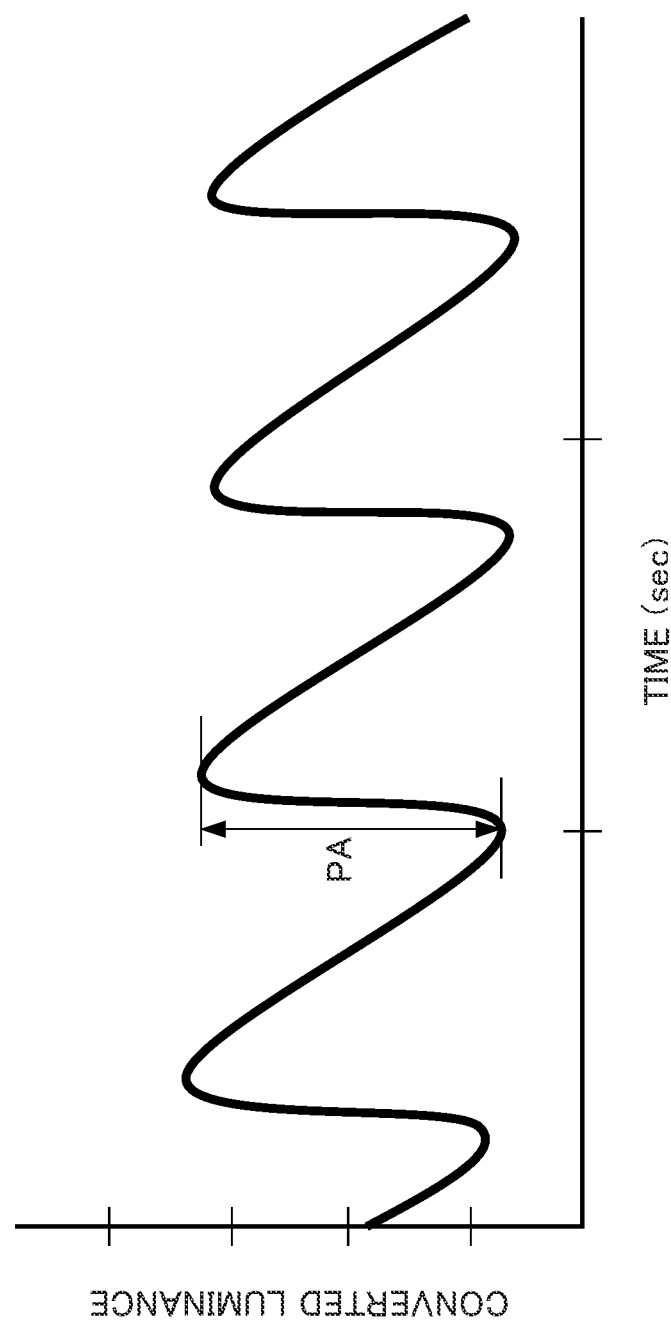

PA LEVEL VALUE

PA LEVEL VALUE

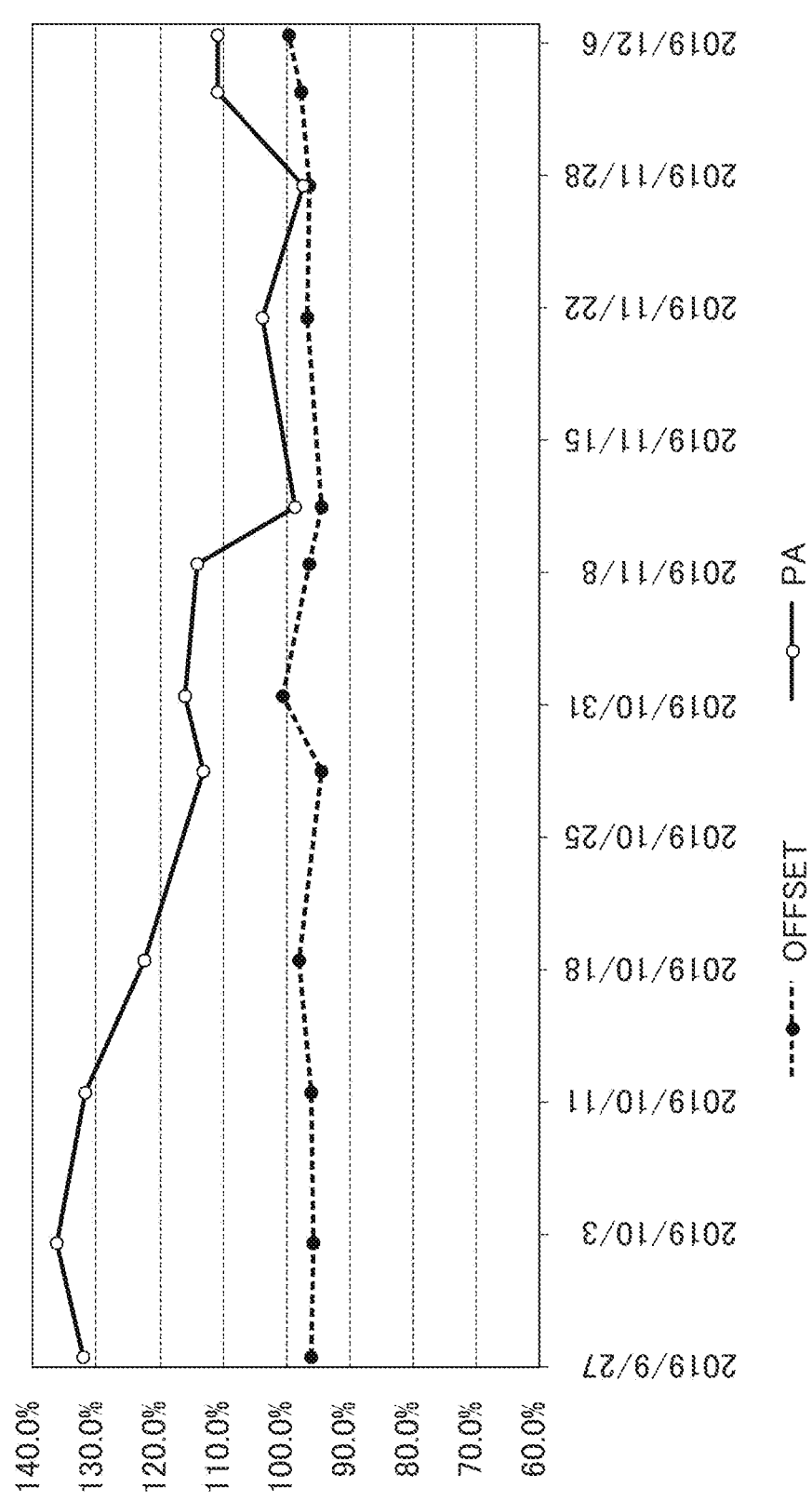

ELECTRONIC DEVICE, CONTROL METHOD FOR THE ELECTRONIC DEVICE, AND STORAGE MEDIUM

This application is based on and claims the benefit of priority from Japanese Patent Application No. 2020-052655, filed on 24 Mar. 2020, the content of which is incorporated herein by reference.

BACKGROUND OF THE INVENTION

Field of the Invention

The present disclosure relates to an electronic device, a control method for the electronic device, and a storage medium.

Related Art

Conventionally, a technique for acquiring biological information such as blood flow of a subject from a video has been known. Japanese Unexamined Patent Application, Publication No. 2016-190022 describes acquiring information relating to a pulse wave of a subject based on luminance information in a video signal, and displaying blood circulation information calculated based on a variation in the pulse wave as a heat map.

SUMMARY OF THE INVENTION

In order to achieve the object of the present invention, an electronic device according an aspect of the present invention includes: memory; and at least one processor, in which the at least one processor executes a program stored in the memory to perform operations including: acquiring, based on video information of a body in a first video obtained by image-capturing at least a portion of the body, first pulse wave amplitude information indicating an amplitude of a pulse wave of the body within a predetermined period of time, acquiring, based on video information of the body in a second video obtained by image-capturing at least a portion of the body after image-capturing the first video, second pulse wave amplitude information indicating an amplitude of a pulse wave of the body within a predetermined period of time, comparing the first pulse wave amplitude information with the second pulse wave amplitude information to output a comparison result indicating a degree of variation in a blood flow, and acquiring a trend in variation of the blood flow based on a comparison result newly outputted by the at least one processor and the comparison result previously stored in the memory.

According to the electronic device, the control method for the electronic device, and the storage medium of the present disclosure, it is possible to precisely measure an effect of a continuously performed cosmetic treatment and the like.

BRIEF DESCRIPTION OF THE DRAWINGS

FIG. 7 is a functional block diagram showing a functional configuration for executing measurement processing among the functional configurations of the electronic device according to the embodiment of the present disclosure;

FIG. 11 is a graph showing the amplitude of a pulse wave measured by an electronic device according to an embodiment of the present disclosure;

FIG. 13 is a graph showing the transitions of ratio of change in actual measurement values of PA level values and a baseline of a blood flow measured by an electronic device according to an embodiment of the present disclosure;

DETAILED DESCRIPTION OF THE INVENTION

Summary of the Embodiments

Embodiments of the present disclosure will be described below with reference to the drawings. An electronic device 1 according to an embodiment of the present disclosure is a smart mirror configured as a self-supporting mirror that can be carried by a user. The electronic device 1 captures an image of a user as a target person who visually recognizes the mirror. The electronic device 1 acquires biological information based on a video captured by the user.

[System Configuration]

Figure 1:
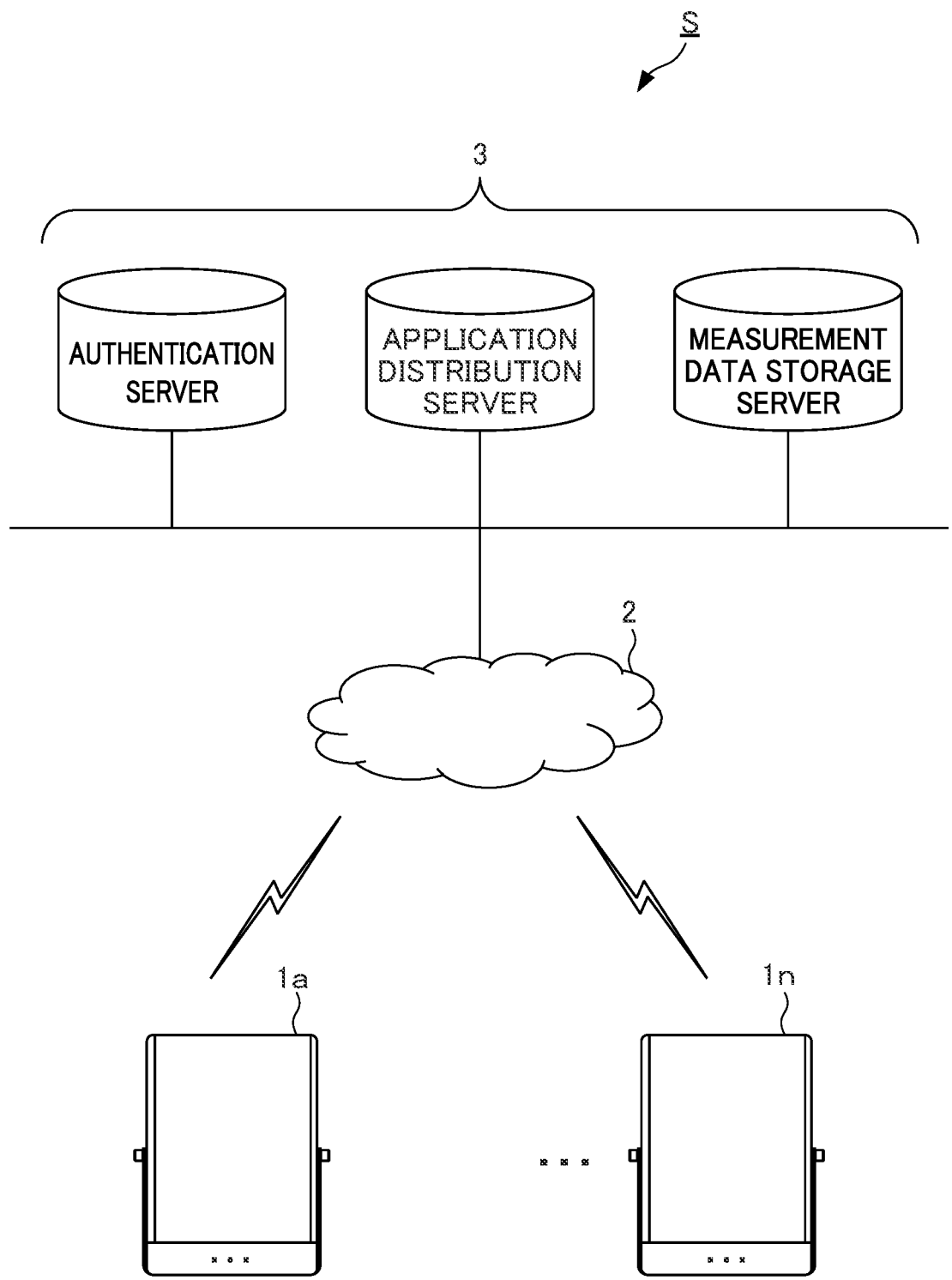
FIG. 1 is a configuration diagram showing a configuration of a measurement system according to an embodiment of the present disclosure.

FIG. 1 is a block diagram showing an overall configuration of a measurement system S including an electronic device 1 according to the present embodiment. As shown in FIG. 1, the measurement system S includes a plurality of electronic devices 1, a network 2, and a server group 3. The number of the electronic devices 1 is not particularly limited, and n-number of electronic devices 1 (n is any natural number) may be included in the display system 1. It should be noted that, in the following description, when the n-number of electronic devices 1 are described without any particular distinction, the letter at the end of the symbol is omitted, and thus these devices are simply referred to as "electronic device 1".

The electronic device 1 is a measurement device that measures blood flow variation of a user from a video and displays a measurement result. The electronic device 1 is connected to each server included in the server group 3 so as to be able to communicate with each other via the network 2.

The network 2 is realized by, for example, the Internet, a LAN (Local Area Network), any of cellular telephone networks, or a combination thereof.

The server group 3 includes various servers that cooperate with the electronic device 1. For example, the server group 3 includes an authentication server for authenticating a user of the electronic device 1. Furthermore, for example, the server group 3 includes an application distribution server that distributes application software for realizing the functions of the electronic device 1.

Furthermore, for example, the server group 3 includes a measurement data storage server that stores profile information of the user, which is information including setting information related to the user, a usage history of the electronic device 1 by the user, and the like.

Figure 2:
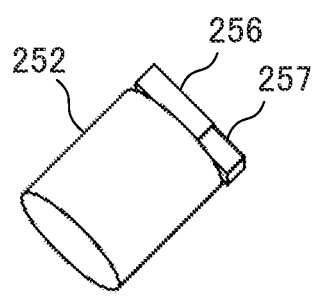
FIG. 2 is a configuration diagram showing a configuration of a measurement-dedicated camera for use in a measurement system according to an embodiment of the present disclosure.

Furthermore, the electronic device 1 is electrically connected to a measurement-dedicated camera 25 by way of wired or wireless communication. FIG. 2 shows a configuration of the measurement-dedicated camera 25. The measurement-dedicated camera 25 includes an imaging unit 256, a dedicated cover 252 that isolates the imaging unit 256 from the outside, and an illumination unit 257 that irradiates a measurement target in the cover 252 with light. By image-capturing the measurement target with a tip of the cover 252 in contact with the measurement target, it is possible to acquire a video in a state in which the influence of disturbance is suppressed and the brightness in the cover is kept constant.

It should be noted that the measurement system S shown in FIG. 1 is merely an example, and a server having another function may be included in the server group 3. Furthermore, a plurality of servers included in the server group 3 may be implemented by a separate server device, or may be implemented by a single server device.

[Exterior Appearance Configuration]

Figure 3:
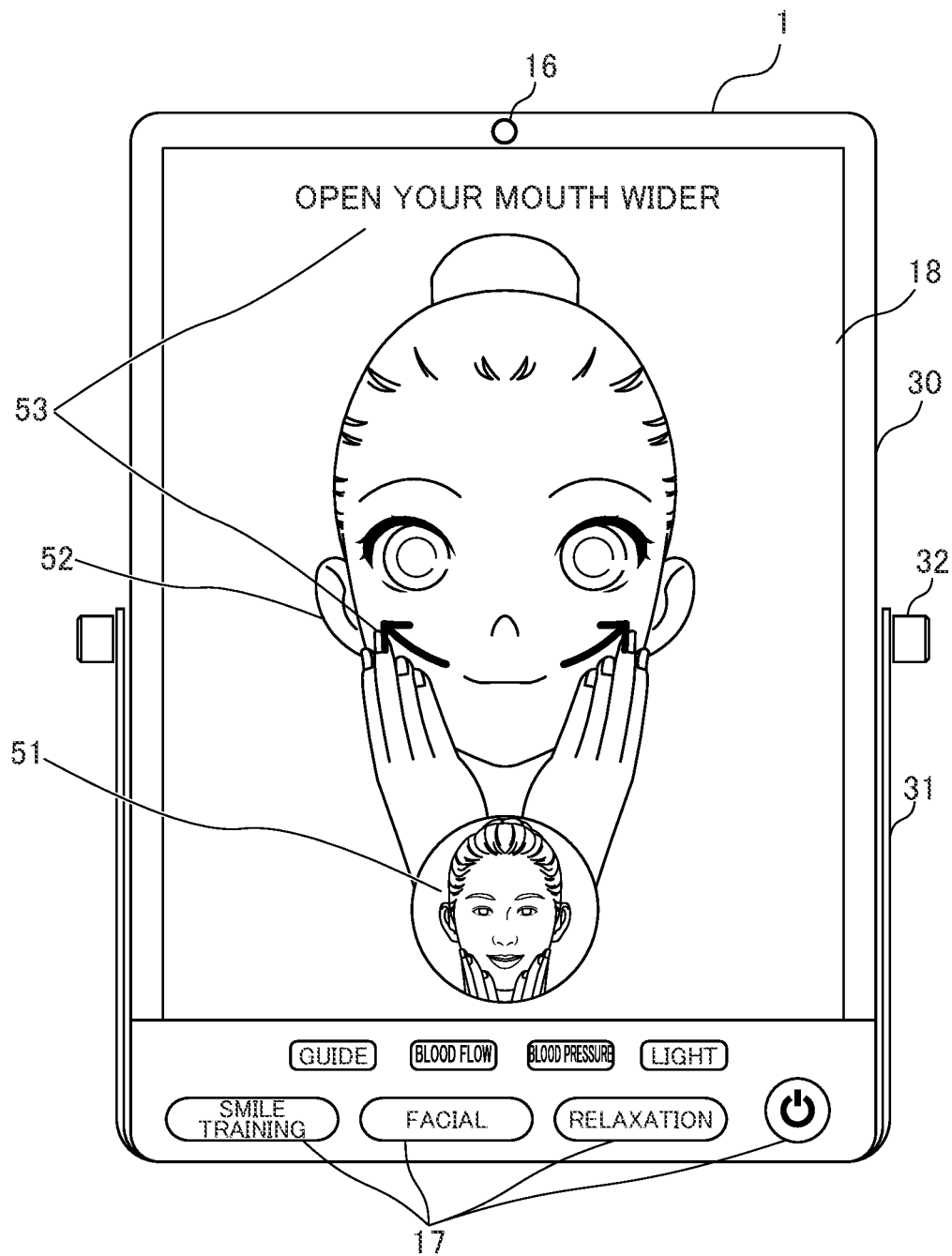
FIG. 3 is a configuration diagram showing an exterior appearance configuration of a front surface of an electronic device according to an embodiment of the present disclosure.
Figure 4A:
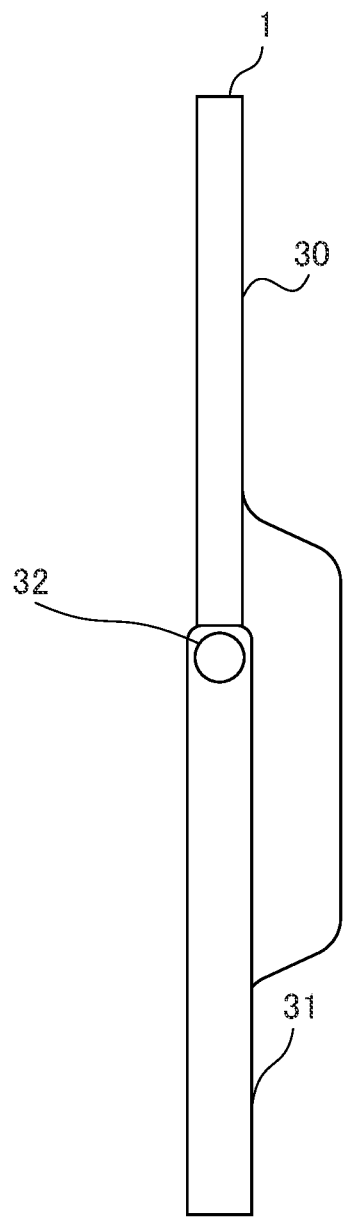
FIG. 4A is a configuration diagram showing an exterior appearance configuration of a side surface of an electronic device according to an embodiment of the present disclosure.
Figure 4B:
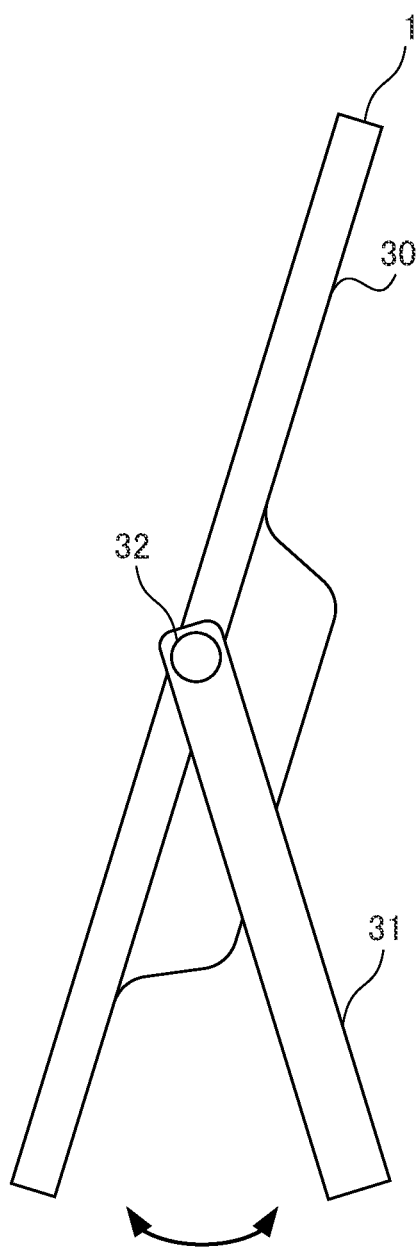
FIG. 4B is a configuration diagram showing an exterior appearance configuration of a side surface of an electronic device according to an embodiment of the present disclosure.

FIG. 3 is a configuration diagram showing an exterior appearance configuration of a front surface of the electronic device 1 according to an embodiment of the present disclosure. Furthermore, FIG. 4A and FIG. 4B are a block diagram showing an exterior appearance configuration of a side surface of the electronic device 1. The size of the front surface of the electronic device 1 is, for example, A4 size defined by ISO (International Organization for Standardization) 216, which is an internationally recognized standard.

As shown in FIG. 3, FIG. 4A and FIG. 4B, the electronic device 1 includes a main body portion 30, a leg portion 31, and a hinge portion 32. The main body portion 30 is a portion including the display unit 18 and other hardware to be described later with reference to FIG. 5. Furthermore, the leg portion 31 and the hinge portion 32 are members for allowing the electronic device 1 to stand freely. The leg portion 31 is rotatably supported with respect to the main body portion 30 by the hinge portion 32.

As shown in FIG. 4A, when carrying the electronic device 1, it is possible for the user to carry the electronic device 1 in a non-bulky form in which the side surface of the main body portion 30 is aligned with the side surface of the leg portion 31. On the other hand, as shown in FIG. 4B, when the user installs and uses the electronic device 1 on a desk or the like, it is possible to install the electronic device 1 independently by rotating the leg portion 31 around the hinge portion 32 as a center point. It should be noted that, in order to allow the electronic device 1 to stand freely, the hinge portion 32 has a mechanism for holding in a state where the leg portion 31 is kept at a predetermined angle.

The main body portion 30 includes the display unit 18 as described above. The display unit 18 is a portion for displaying these various kinds of information to the user by displaying various kinds of information. The display unit 18 displays, for example, a user image (corresponding to a user image 51 in the figure) which is a real image of the user captured by the imaging unit 16 as a subject, an avatar image (corresponding to an avatar image 52 in the figure) which is a substitute image for the user, and a guide image (corresponding to a guide image 53 in the figure) which is auxiliary information for performing guidance. Furthermore, in this case, the guide image is composited with the avatar image and displayed in a superimposed manner on the display unit 18.

The user can grasp these various pieces of information at a time by visually recognizing the display unit 18. It should be noted that the display of the display unit 18 as described above has a sense of unity suitable for the user to visually recognize without a visual gap.

As shown in FIG. 3, the electronic device 1 further includes an imaging unit 16, an input unit 17, and the display unit 18, as an exterior appearance configuration.

The imaging unit 16 is a camera for capturing a user facing the display unit 18 as a subject during the use of the electronic device 1. The imaging unit 16 is disposed at a position where the user image 51 including the face of the user directly facing the display unit 18 can be captured. For example, as shown in the drawing, the imaging unit 16 is disposed on the front surface of the main body portion 30 and on the upper portion of the display unit 18.

It should be noted that it is possible for the electronic device 1 to use both the imaging unit 16 and the above-described measurement-dedicated camera 25 in order to image-capture the user image 51. More specifically, it is possible for the electronic device 1 to selectively use either one of the imaging unit 16 or the measurement-dedicated camera 25, or use both depending on its use.

The input unit 17 is a unit for receiving an operation input by a user. The input unit 17 is realized by a plurality of buttons, for example. In the drawing, as an example, buttons for switching to various modes such as small face beauty treatment, smile training, and recording of biometric information, and a button for switching on/off the power of the electronic device 1 are illustrated.

The external structure of the electronic device 1 has been described above. However, this structure is merely an example, and the external structure of the electronic device 1 is not limited to this example.

For example, the electronic device 1 may further include a light emitting unit that emits light to illuminate the user facing the display unit 18. The light emitting unit illuminates the user by adjusting the illuminance and color components. Therefore, the electronic device 1 functions as a mirror with illumination. A plurality of light emitting units may be provided. Furthermore, the light emitting unit may be disposed at the upper portion or the lower portion of the display unit 18, or may be disposed over the entire periphery of the display unit 18.

Furthermore, for example, the number and arrangement of the input units 17 may be changed. Furthermore, for example, a part of the display unit 18 may be configured as a touch screen, and the input unit 17 and the display unit 18 may be integrally configured.

[Hardware Configuration]

Figure 5:
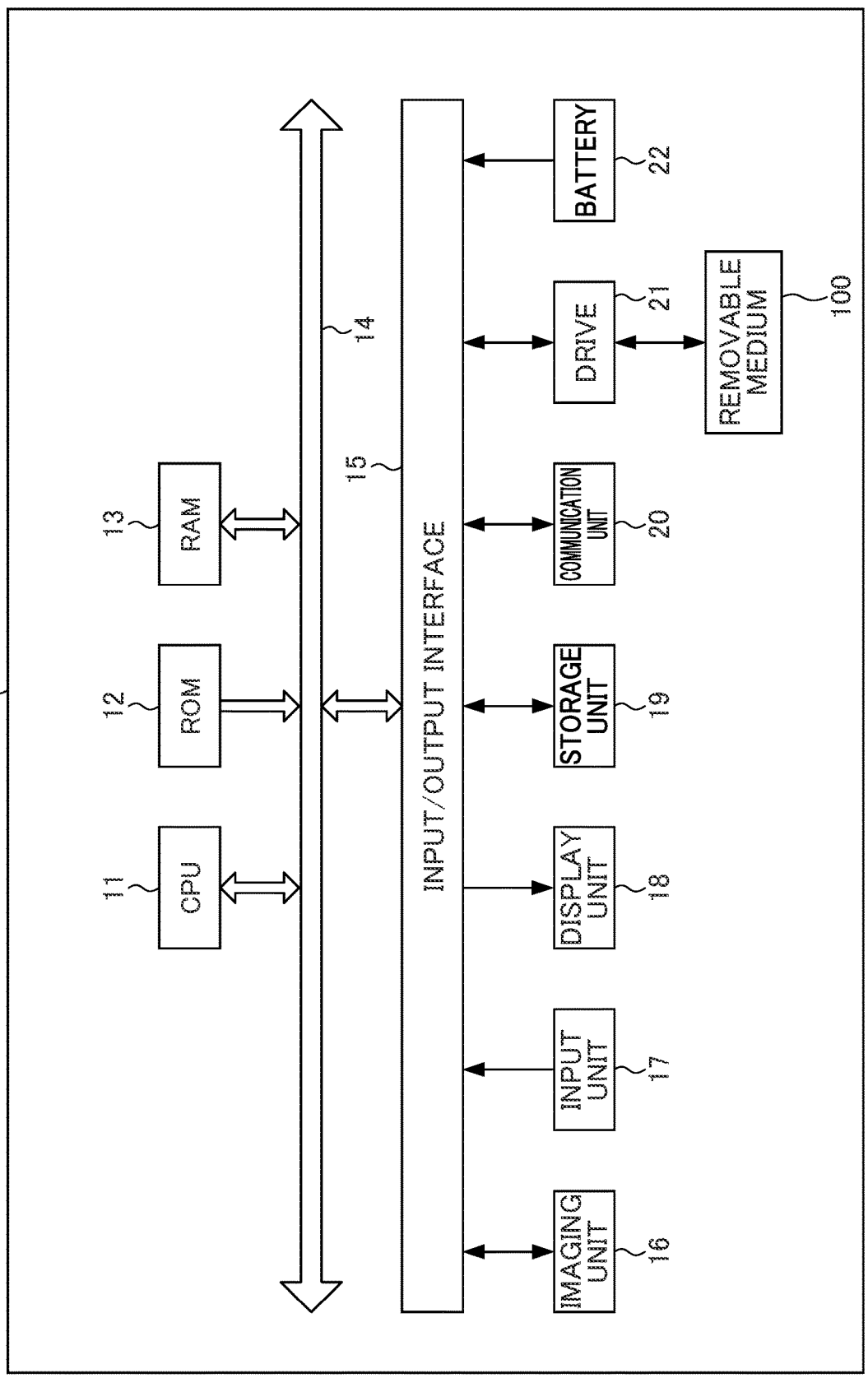
FIG. 5 is a block diagram showing a hardware configuration of an electronic device according to an embodiment of the present disclosure.

FIG. 5 is a block diagram illustrating a hardware configuration of the electronic device 1. As illustrated in FIG. 5, the electronic device 1 includes a central processing unit (CPU) 11 which is a processer, a read only memory (ROM) 12, a random access memory (RAM) 13, a bus 14, an input/output interface 15, an imaging unit 16, an input unit 17, a display unit 18, a storage unit 19, a communication unit 20, a drive 21 and a battery 22.

The CPU 11 executes various processings according to a program recorded in the ROM 12, or a program loaded in the RAM 13 from the storage unit 19.

Data or the like necessary for the CPU 11 to execute various processings, is also suitably stored in the RAM 13.

The CPU 11, the ROM 12, and the RAM 13 are connected to each other through the bus 14. In addition, the input/output interface 15 is also connected to the bus 14. The imaging unit 16, the input unit 17, the display unit 18, the storage unit 19, the communication unit 20, the drive 21 and the battery 22 are connected to the input/output interface 15.

Although not illustrated, the imaging unit 16 includes an optical lens unit and an image sensor. The optical lens unit includes a lens such as, for example, a focus lens, a zoom lens, or the like that collects light in order to photograph a subject. The focus lens is a lens that forms a subject image on a light receiving surface of the image sensor. The zoom lens is a lens that causes a focal length to be freely changed within a certain range. Further, a peripheral circuit for adjusting setting parameters such as focus, exposure, white balance, and the like is installed in the imaging unit 16 if necessary.

The image sensor is configured of a photoelectric conversion element, an analog front end (AFE), or the like. The photoelectric conversion element, for example, is configured of a complementary metal oxide semiconductor (CMOS) type photoelectric conversion element or the like. The subject image is incident on the photoelectric conversion element from the optical lens unit. Then, the photoelectric conversion element performs photoelectric conversion (imaging) with respect to the subject image, accumulates an image signal for a constant time, and sequentially supplies the accumulated image signals to the AFE, as an analog signal. The AFE executes various signal processings such as analog/digital (A/D) conversion processing, with respect to the analog image signal. A digital signal is generated by the various signal processings, and is output as an output signal from the imaging unit 16. Such output signal from the imaging unit 16 is appropriately supplied to the CPU 11 or the like.

The input unit 17 includes various types of buttons, microphones or the like, and inputs various types of information in accordance with an instruction manipulation or an instruction voice of the user.

The display unit 18 includes a liquid crystal display or the like, and displays an image corresponding to image data output from the CPU 11.

The storage unit 19 includes a semiconductor memory such as a dynamic random access memory (DRAM) and stores various types of data.

In the communication unit 20, the CPU 11 performs communication control for performing communication with other devices (for example, the servers included in the server group 3) via the network 2.

The drive 21 is constituted by an interface onto which a removable medium 100 can be loaded. The removable medium 100 including a magnetic disk, an optical disk, a magneto-optical disk, a semiconductor memory or the like is properly loaded onto the drive 21. The removable medium 100 stores a program for executing a composition display process to be described later or various types of data such as image data. The program or various types of data such as image data read from the removable medium 100 by the drive 21 is installed in the storage unit 19 if necessary.

The battery 22 supplies power to each part of the device and and is configured to be rechargeable when connected to an external power source. When the electronic device 1 is not connected to an external power supply, the electronic device 1 operates by the power of the battery 22.

The electronic device 1 may further include another hardware in addition to the hardware described above. For example, the electronic device 1 includes a lamp, a speaker, a vibration motor, or the like, and may include an output section that outputs light, a sound, or a vibration signal.

Figure 6:
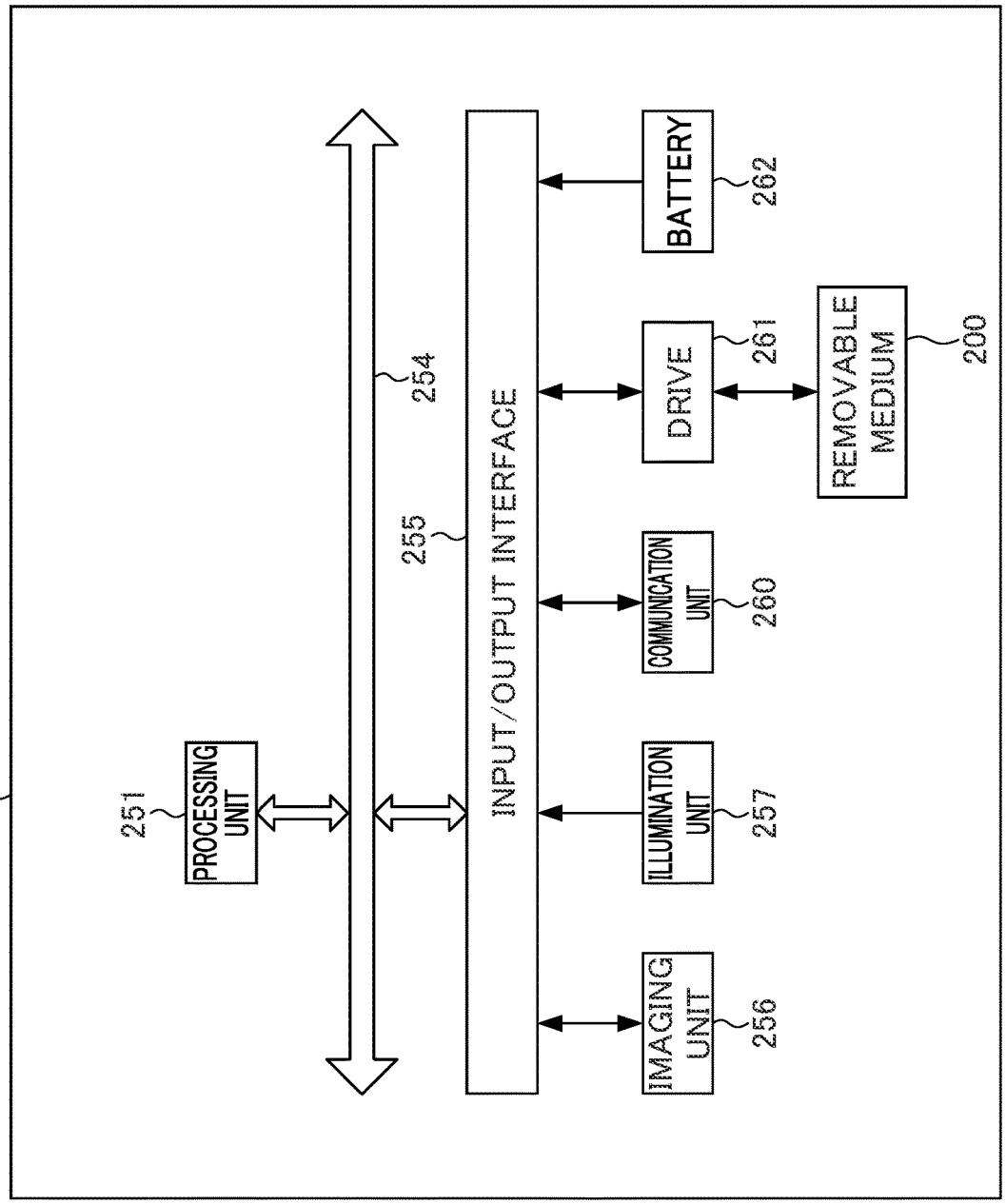
FIG. 6 is a block diagram showing a hardware configuration of the measurement-dedicated camera for use in an electronic device according to an embodiment of the present disclosure.

FIG. 6 is a block diagram showing the hardware configuration of the measurement-dedicated camera 25. As shown in FIG. 6, the measurement-dedicated camera 25 includes a processing unit 251, the imaging unit 256, the illumination unit 257, a communication unit 260, a drive 261, and a battery 262.

The processing unit 251 controls the entire measurement-dedicated camera 25. Specifically, the processing unit 251 communicates with the CPU 11 of the electronic device 1 through the communication unit 260 to be described later, and acquires a command signal from the electronic device 1, thereby controlling the entire measurement-dedicated camera 25. It should be noted that the control of the entire measurement-dedicated camera 25 includes the processing of the video captured by the imaging unit 256 to be described later.

Although not shown, the imaging unit 256 includes an optical lens unit and/or an image sensor. In order to capture an image of a subject, the optical lens unit includes a lens such as a focus lens for condensing light and a zoom lens. The focus lens is a lens for forming an image of a subject on the light receiving surface of the image sensor. The zoom lens is a lens that causes the focal length to freely change in a certain range. The imaging unit 256 also includes peripheral circuits to adjust setting parameters such as focus, exposure, white balance, and the like, as necessary.

The image sensor is configured by an optoelectronic conversion device, an AFE (Analog Front End), and the like. The optoelectronic conversion device is configured by a CMOS (Complementary Metal Oxide Semiconductor) type of optoelectronic conversion device and the like, for example. Light incident through the optical lens unit forms an image of a subject in the optoelectronic conversion device. The optoelectronic conversion device optoelectronically converts (i.e. captures) the image of the subject, accumulates the resultant image signal for a predetermined time interval, and sequentially supplies the image signal as an analog signal to the AFE. The AFE executes a variety of signal processing such as A/D (Analog/Digital) conversion processing of the analog signal. The variety of signal processing generates a digital signal that is output as an output signal from the imaging unit 256. Such an output signal from the imaging unit 256 is appropriately supplied to the processing unit 251, etc.

When the imaging unit 256 images, the illumination unit 257 applies light to the field of view of the imaging unit 256 according to the control signal from the processing unit 251. The illumination unit 257 can be realized by, for example, an LED and a light control circuit.

The communication unit 260 performs communication control for the processing unit 251 communicating with the electronic device 1.

The drive 261 includes an interface through which a removable medium 200 can be mounted. For example, the removable medium 200 including semiconductor memory such as USB (Universal Serial Bus) memory is appropriately mounted to the drive 261. The removable medium 200, for example, stores various data such as image data and programs for use in the processing by the processing unit 251.

The battery 262 supplies power to each component, and is chargeable by connecting to an external power supply. When the measurement-dedicated camera 25 is not connected to the external power supply, the electronic device 1 operates with the power from the battery 262.

It should be noted that the measurement-dedicated camera 25 may further include other hardware in addition to the above-described hardware.

[Functional Configuration]

FIG. 7 is a functional block diagram showing a functional configuration for executing measurement processing among the functional configurations of the electronic device 1. The measurement processing refers to a series of processing in which the electronic device 1 displays the measurement result based on the variation in the biological information value acquired from the user.

First, the storage unit 19 for storing various kinds of information will be described. The storage unit 19 stores various types of data relating to guidance in the display processing, various types of data relating to avatars as substitutes for the real image of the user, information for performing measurement, information for displaying the measurement result, information indicating the measurement result, and the like. It should be noted that the above-described various types of data may be stored only in the storage unit 19, or may be stored as appropriate in the removable medium 100 by the drive 21. Furthermore, each piece of information may be stored as appropriate in the measurement data storage server or the like included in the server group 3.

Next, each functional block for executing the measurement processing will be described. As shown in FIG. 7, a video processing unit 111, a display processing unit 112, a result processing unit 113, an evaluation processing unit 114, an information processing unit 115, and a communication processing unit 116 function in the CPU 11 as the control unit.

The video processing unit 111 analyzes a video including the user as a subject captured by the imaging unit 16, thereby acquiring information about the user (hereinafter referred to as "subject information"). Examples of the subject information include coordinates indicating the position of each portion in the face or the like of the user image 51, the color of each portion in the face or the like of the user image 51, biometric information indicating the state of the user (sometimes referred to as vital data), or the like. Since the measurement is performed based on the information (video) acquired by the imaging unit 16, the biometric information can be sequentially acquired without touching the user.

Coordinate information as a precondition for performing measurement processing will be described. The coordinate information includes, for example, information for defining each coordinate system, such as an imaging coordinate system that is a coordinate system for an image captured by the imaging unit 16, a display unit coordinate system that is a coordinate system for a display surface of the display unit 18, and information indicating a corresponding relationship for converting coordinates in each coordinate system to coordinates in another coordinate system. Each functional block can perform display processing by transforming coordinates in each coordinate system based on the corresponding relationship of coordinates in each coordinate system. The corresponding relationship of these coordinate systems is set by performing calibration with correction of the corresponding relationship by, for example, the direction adjustment of an imaging lens in the imaging unit 16, or the adjustment of the zoom ratio, etc., at the time of manufacturing the electronic device 1. For example, the adjustment of the zoom ratio is performed using either or both of so-called optical zoom performed by the adjustment of a lens position of the imaging unit 16 and a so-called digital zoom in the image processing.

Furthermore, the video processing unit 111 acquires first pulse wave amplitude information indicating an average amplitude within a predetermined period of time of a wave pulse of a body based on video information of the body in a first video acquired by image-capturing at least a portion of the body, and acquires second pulse wave amplitude information indicating an average amplitude within a predetermined period of time of a pulse wave of the body based on video information of the body in a second video acquired by image-capturing at least a portion of the body after image-capturing the first video. It should be noted that the video processing unit 111 acquires the first pulse wave amplitude information and the second pulse wave amplitude information, each indicating the average amplitude within a predetermined period of time of the pulse wave of a body. However, the present disclosure is not limited thereto. For example, as the first pulse wave amplitude information and the second pulse wave amplitude information, the video processing unit 111 may acquire amplitude information calculated by various kinds of methods such as a most frequent value, a median value, and an average value of an amplitude within a predetermined period.

For example, when a user performs a massage on the user's face, etc., the video processing unit 111 acquires the first pulse wave amplitude information indicating an average amplitude of a pulse wave of the face, etc. within a predetermined period of time based on an image in which the face before the massage is captured, and acquires the second pulse wave amplitude information indicating an average amplitude of a pulse wave of the face, etc. within a predetermined period of time based on an image in which the face after the massage is captured. It should be noted that the definition of "pulse wave" will be provided later.

The display processing unit 112 performs control to display a moving image as a display video. With such a configuration, the blood flow variation can be visualized dynamically, and the difference between before and after a specific action can be displayed in an easy-to-understand manner. The moving image according to the present embodiment is a hue moving image representing the measurement result by a hue. The hue moving image shows a state in which a specific portion (first portion) is divided into small areas in the shape of a square, and the blood flow variation is represented by a variation in hue for each small area. The specific portion is, for example, a part of the face.

Furthermore, the display processing unit 112 also performs composition processing for compositing a guide image and an avatar image. For example, the display processing unit 112 controls the display unit 18 to display a mirror image of the user or an image (e.g., avatar) corresponding to the user. For example, the display processing unit 112 executes processing for switching between a first display mode in which a user image is displayed as a main image and in which an avatar image and a guide image are composited and the resulting composite image is displayed as a sub image, and a second display mode in which the user image is displayed as a sub image and in which the avatar image and the guide image are composited and the resulting composite image is displayed as a main image. As shown in FIG. 3, the avatar image and the guide image, which are composite images, can be displayed in a large size at the center of the screen as a main image, and the user image can be displayed in a smaller size at the bottom of the screen or the like as a sub image. Conversely, the user image may be displayed in a larger size at the center of the screen as a main image, and the avatar image and the guide image, which are composite images, may be displayed in a smaller size at the bottom of the screen or the like as a sub image.

The result processing unit 113 compares the above-described first pulse wave amplitude information with the second pulse wave amplitude information, and outputs a comparison result indicating the degree of variation in a blood flow.

For example, when a user performs a massage on the user's face, etc., the result processing unit 113 compares the first pulse wave amplitude information acquired from the image in which the face before the massage, etc. is captured, with the second pulse wave amplitude information acquired from the image in which the face after the massage, etc. is captured, and outputs a comparison result indicating the degree of variation in a blood flow of the user's face, etc.

Furthermore, when outputting the above-described comparison result, the result processing unit 113 outputs the comparison result to at least the storage unit 19. This allows the storage unit 19 to store a history of the comparison results between the first pulse wave amplitude information and the second pulse wave amplitude information.

The evaluation processing unit 114 acquires a trend in variation of the blood flow based on the comparison result newly outputted by the result processing unit 113 and a previous comparison result stored in the storage unit 19.

For example, when the user performs a massage on the user's face, etc., the evaluation processing unit 114 can acquire a trend in variation of the blood flow before and after the massage based on the newly outputted comparison result with the previous comparison result, and evaluate whether the massage is continuously performed based on the trend in variation of this blood flow. More specifically, in a case in which the user already performed a massage once or more using the electronic device 1, whereby the comparison result between the first pulse wave amplitude information with the second pulse wave amplitude information before and after the massage is stored in the storage unit 19, and the user performs a massage again, if the pulse wave amplitude of the first pulse wave amplitude information before massage is equal to or less than the pulse wave amplitude of the second pulse wave amplitude information after massage, the evaluation processing unit 114 can determine that the massage is continuously performed.

Furthermore, at this time, the evaluation processing unit 114 may acquire a trend in variation of the blood flow based on the comparison result newly outputted by the result processing unit 113 and a most recent and single comparison result stored in the storage unit 19. Alternatively, the evaluation processing unit 114 may acquire a trend in variation of the blood flow based on the comparison result newly outputted by the result processing unit 113 and a plurality of comparison results stored in the storage unit 19. When using the plurality of comparison results stored in the storage unit 19, for example, the difference between the pulse wave amplitude of the first pulse wave amplitude information and the pulse wave amplitude of the second pulse wave amplitude information, or the maximum value, and/or the minimum value, and/or the average value of the ratio of change may be calculated, and the calculated result may be used as the plurality of comparison results.

The information processing unit 115 performs control such as setting relating to measurement processing and display processing. The information processing unit 115 acquires a measurement result indicating a variation in blood flow based on data analysis of the video processing unit 111, the result processing unit 113, and the evaluation processing unit 114.

Furthermore, the information processing unit 115 acquires application software for performing display processing from the application distribution server included in the server group 3, and operates the application software. In addition, the information processing unit 115 receives selection of any guidance content from the user who has referred to the menu displayed on the display unit 18 via an input unit 17 or the like. For example, the information processing unit 115 receives the selection of "small face beauty treatment". In response, the display processing is performed for guidance in relation to small face beauty treatment. It should be noted that the small face beauty treatment means, for example, that a user performs lymph massage or the like on the user's face by himself/herself to reduce the swelling of the face by massage to flow lymph.

The communication processing unit 116 communicates with, for example, an authentication server included in the server group 3. Thus, the user performing the display processing is authenticated. Furthermore, the communication processing unit 116 updates the profile information of the user in the display processing by communicating with, for example, the measurement data storage server included in the server group 3.

[Analysis of Video Data]

First, the acquisition of video data analyzed by the video processing unit 111 will be described.

The video processing unit 111 performs processing relating to face tracking such as pattern matching of contours and regions, skin color identification, and the like, thereby recognizing the contours of the face, the positions of eyes, and regions of the skin, and detecting predetermined region regions such as the forehead, cheek, jaw, and neck. For example, a face contour and an eye position are detected from the user image 51 in the video image, and a plurality of regions such as forehead, an eyelid, a cheek, a nasal periphery, a lip periphery, a jaw, a neck, and a low-necked portion are automatically recognized based on the relative positions thereof. Furthermore, the video processing unit 111 detects the coordinates and the skin color of the user of each of the detected regions, and the angle of the face of the user image 51, i.e., the direction of the user's face.

The video processing unit 111 uses the property that the hemoglobin in the blood absorbs green light well to extract the pulse wave from the video, and acquires the biological information about the blood flow such as the pulse and the pulse wave. The wavelength of the green signal is generally considered to be 495-570 nm, and hemoglobin has a high absorption coefficient around 500-600 nm. When the blood flow rises, the amount of blood increases on the skin surface and the amount of hemoglobin per unit time increases, so that more green signals are absorbed by the hemoglobin than before the blood flow rises. Therefore, the luminance of the green signal detected when the blood flow rises decreases. It should be noted that, when an imaging device of the imaging unit 16 converts the light into luminance, an RGB filter is provided in front of the imaging device, and the luminance value of each pixel for the respective RGBs is calculated. In this case, the light passing through the green filter becomes the luminance value. Even if the sensitivity of the imaging device is flat with respect to the wavelength, since the wavelength band can be narrowed down accurately to some extent by the filter described above, it is possible to detect the green signal.

The video processing unit 111 acquires pulse wave information based on the luminance information included in the video information of a body in the video. More specifically, the video processing unit 111 acquires the pulse wave information from the temporal change in luminance of the green signal by acquiring the luminance of the green signal for each unit time. It should be noted that the unit time is, for example, a frame rate of the moving image, and it is possible to acquire the luminance of the green signal for each image which is consecutively present in time to constitute the video.

In the present embodiment, in order to make it easier to grasp the increase of the blood flow in a sensory manner, conversion processing is performed so that the luminance value becomes high when the blood flow rises. More specifically, when the luminance of the green signal is detected using an image sensor of the output of 8 bits of each RGB color, a numerical value obtained by subtracting a detected luminance value of the green signal from the maximum value 255 of the luminance value is used as "converted luminance" for comparison processing. What is simply described as the converted luminance hereinafter is information about the luminance subjected to such conversion processing.

In order to compare the states of the blood flow before and after the event of the user, the electronic device 1 acquires a first video by imaging the user before the event and acquires a second video by imaging the user after the event.

The event is, for example, a massage for promoting blood flow, various cosmetic treatments such as application of skin cream promoting blood circulation, or various actions in which a change in blood flow is predicted such as exercise such as sports or relaxation.

FIGS. 8A to 8D each shows a temporal change in an RGB luminance value in the first video before and after a massage as an event, and a temporal change in the RGB luminance value in the second image before and after a massage.

Figure 8A:
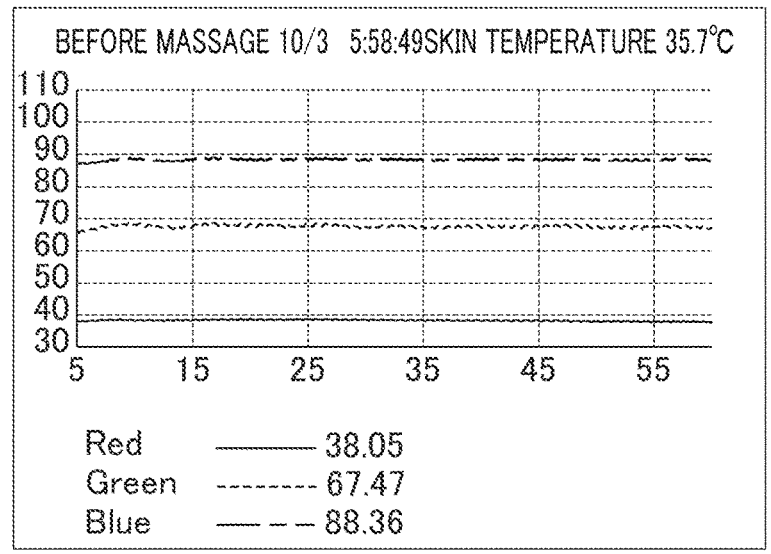
FIG. 8A is a graph showing a temporal change in an RGB luminance value before and after a massage measured by an electronic device according to an embodiment of the present disclosure.
Figure 8B:
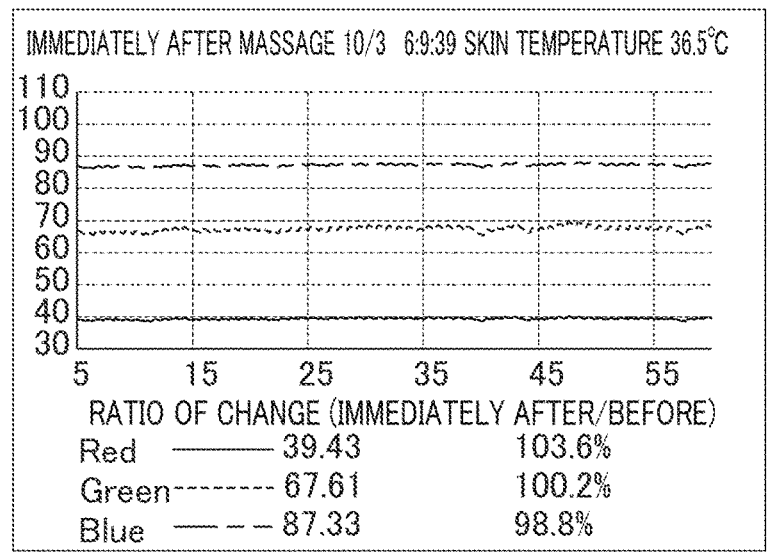
FIG. 8B is a graph showing a temporal change in an RGB luminance value before and after a massage measured by an electronic device according to an embodiment of the present disclosure.
Figure 8C:
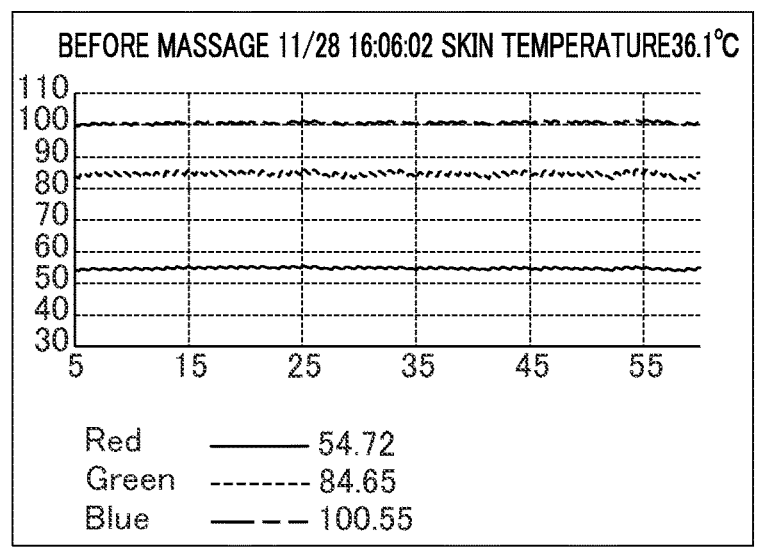
FIG. 8C is a graph showing a temporal change in an RGB luminance value before and after a massage measured by an electronic device according to an embodiment of the present disclosure.

More specifically, FIG. 8A shows, as an example, a temporal change in the RGB luminance values before massage on October 3 when massage is started. Furthermore, FIG. 8B shows a temporal change in the RGB luminance value after massage on October 3, which is the same day. Furthermore, FIG. 8C shows a temporal change in the RGB luminance value before massage on November 28, which is about two months later from the time of FIG. 8A and FIG.

Figure 8D:
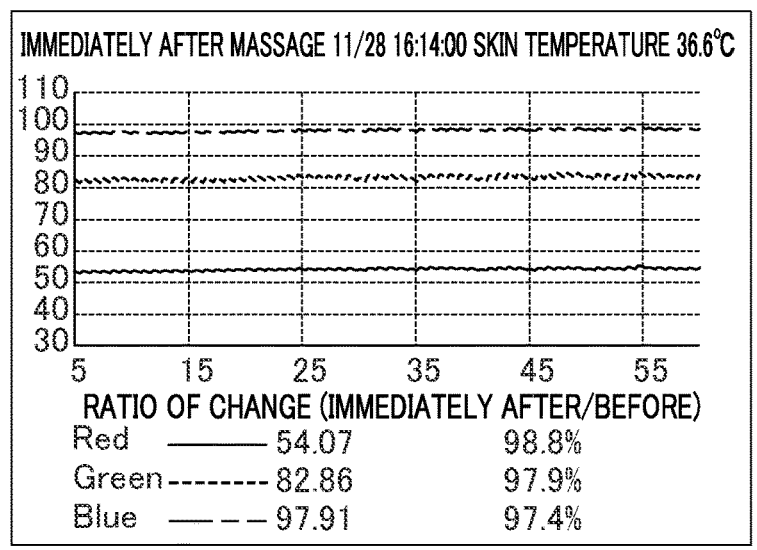
FIG. 8D is a graph showing a temporal change in an RGB luminance value before and after a massage measured by an electronic device according to an embodiment of the present disclosure.
Figure 9A:
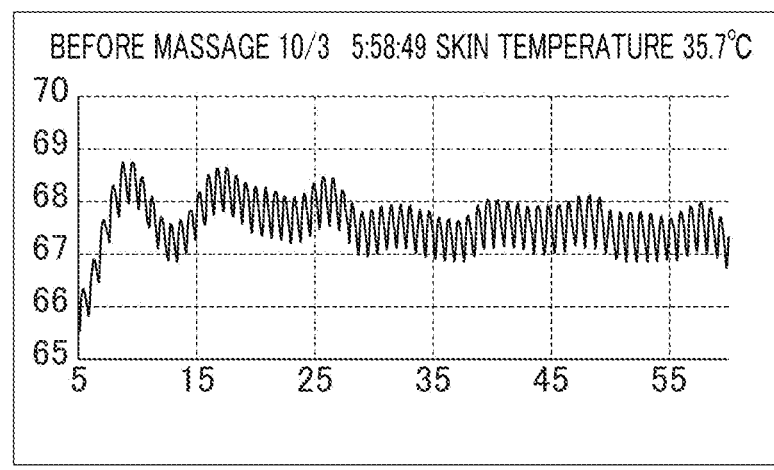
FIG. 9A is a graph showing a temporal change in a G luminance value before and after a massage measured by an electronic device according to an embodiment of the present disclosure.
Figure 9B:
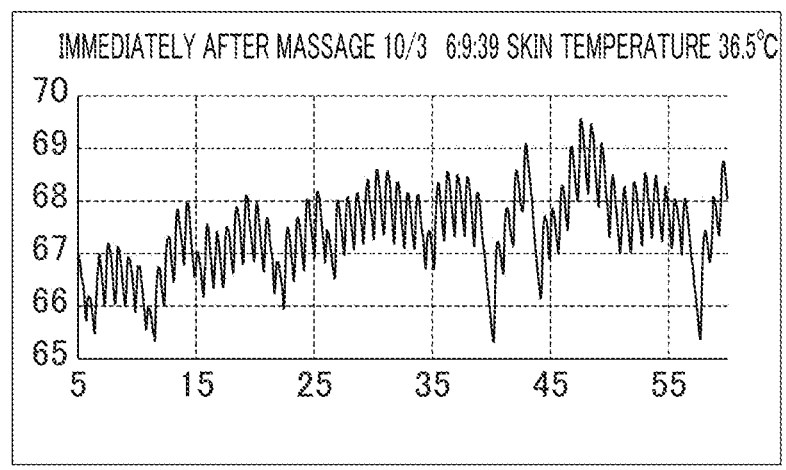
FIG. 9B is a graph showing a temporal change in a G luminance value before and after a massage measured by an electronic device according to an embodiment of the present disclosure.
Figure 9C:
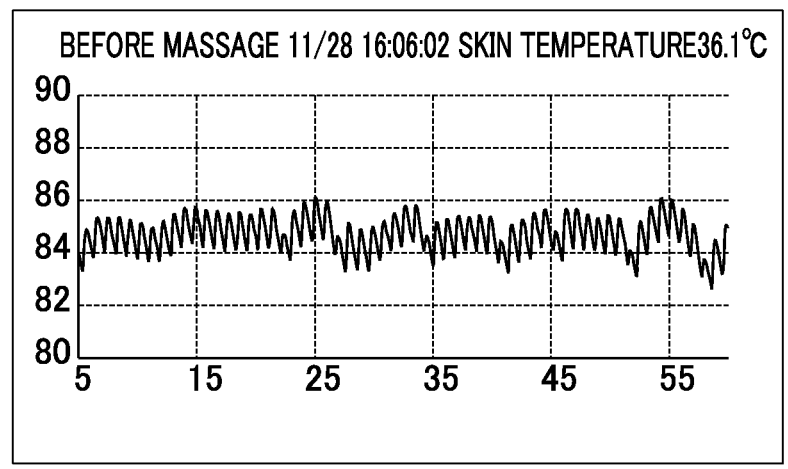
FIG. 9C is a graph showing a temporal change in a G luminance value before and after a massage measured by an electronic device according to an embodiment of the present disclosure.
Figure 9D:
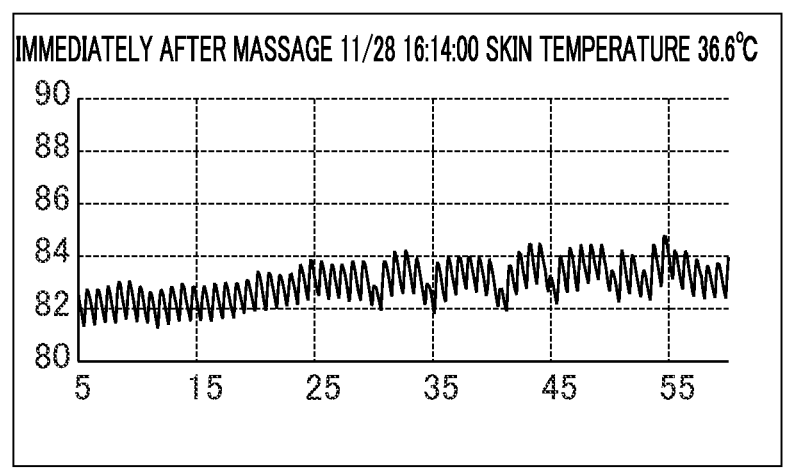
FIG. 9D is a graph showing a temporal change in a G luminance value before and after a massage measured by an electronic device according to an embodiment of the present disclosure.
Figure 10A:
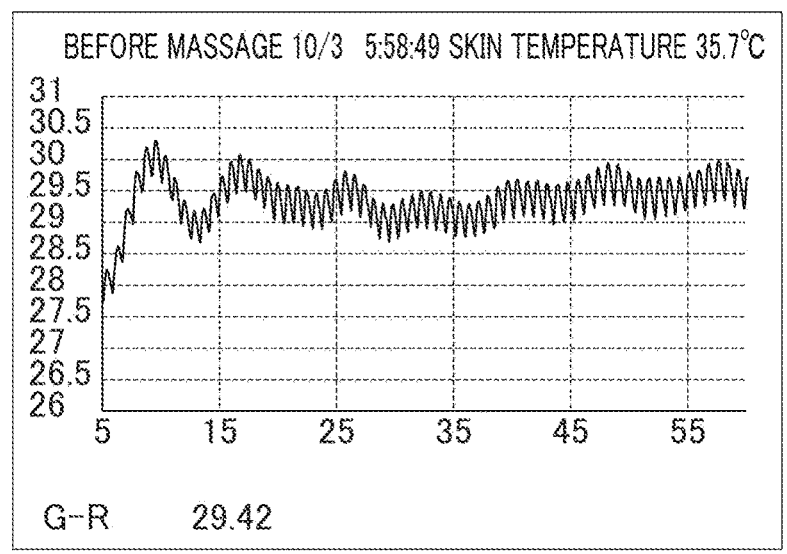
FIG. 10A is a graph showing a temporal change in a G-R value before and after a massage measured by an electronic device according to an embodiment of the present disclosure.
Figure 10B:
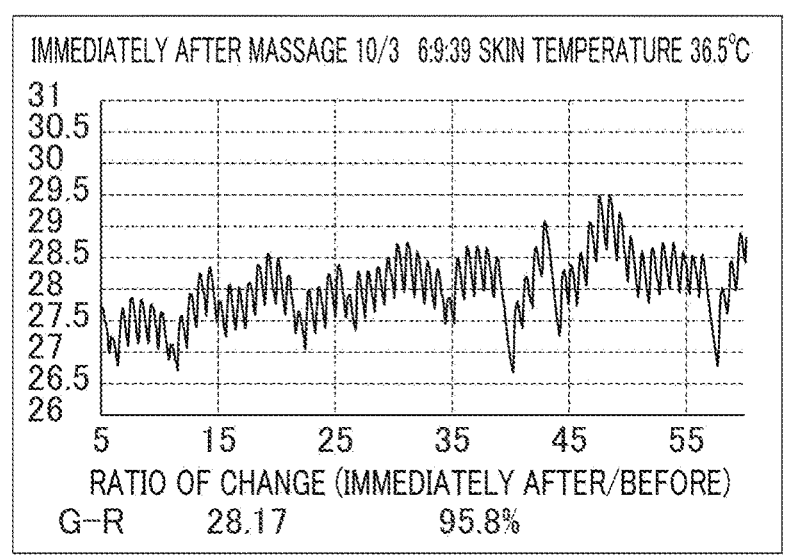
FIG. 10B is a graph showing a temporal change in a G-R value before and after a massage measured by an electronic device according to an embodiment of the present disclosure.
Figure 10C:
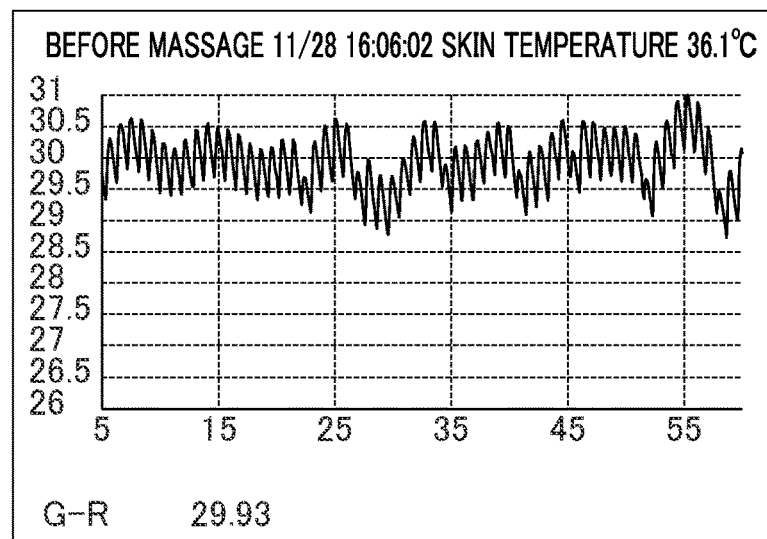
FIG. 10C is a graph showing a temporal change in a G-R value before and after a massage measured by an electronic device according to an embodiment of the present disclosure.
Figure 10D:
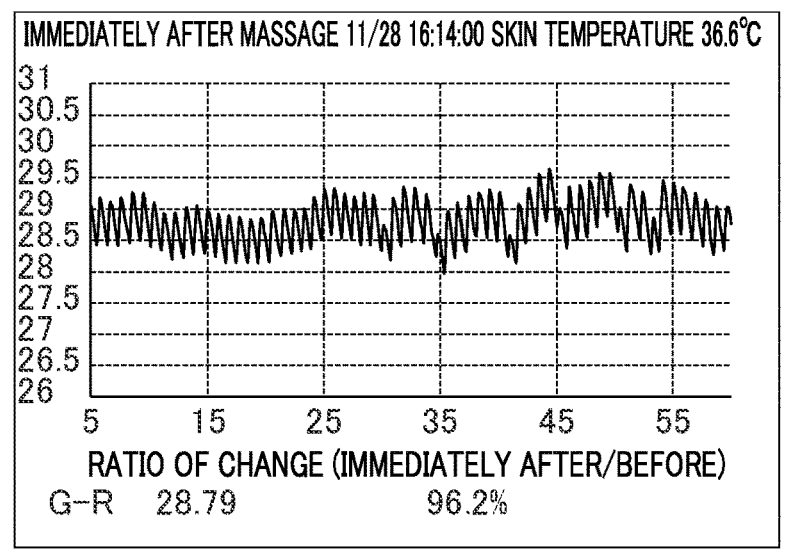
FIG. 10D is a graph showing a temporal change in a G-R value before and after a massage measured by an electronic device according to an embodiment of the present disclosure.
Figure 12A:
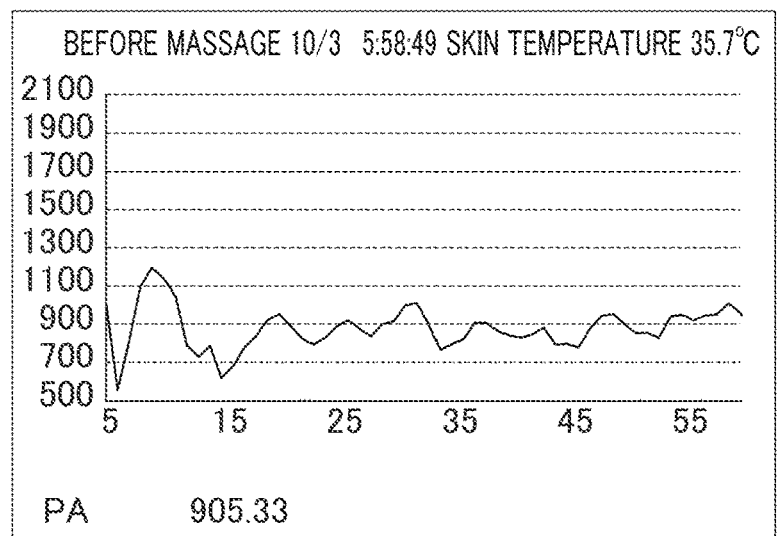
FIG. 12A is a graph showing a temporal change in a PA level value before and after a massage measured by an electronic device according to an embodiment of the present disclosure.
Figure 12B:
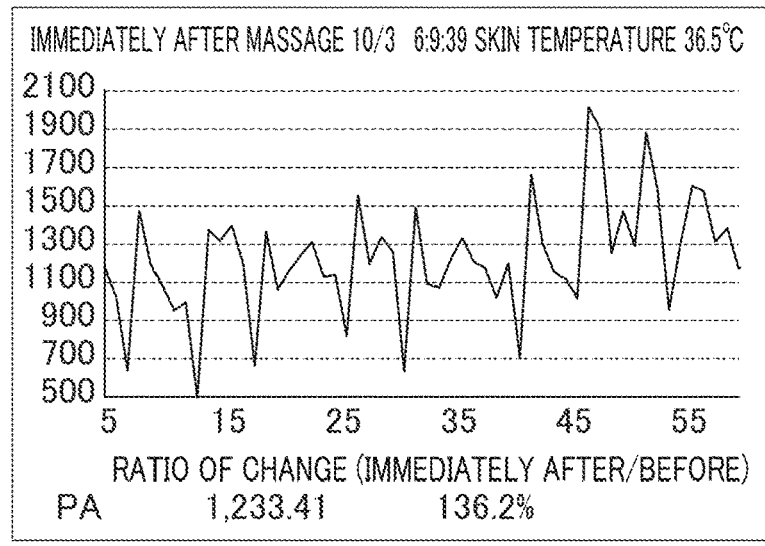
FIG. 12B is a graph showing a temporal change in a PA level value before and after a massage measured by an electronic device according to an embodiment of the present disclosure.
Figure 12C:
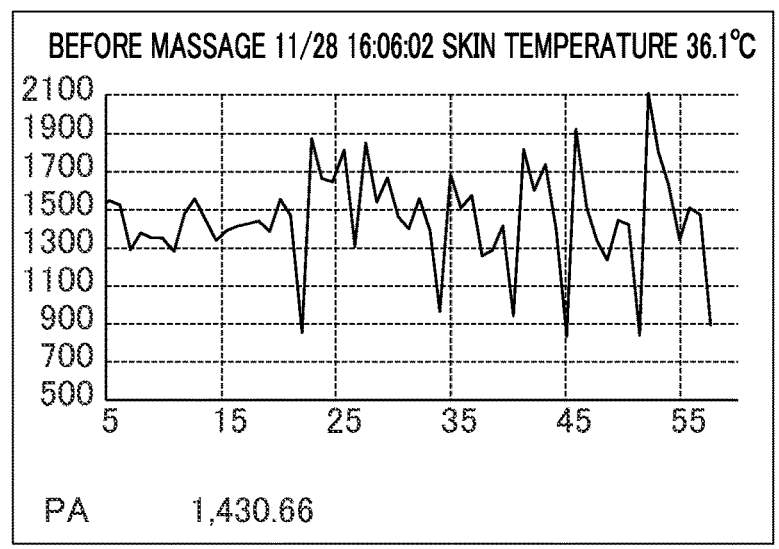
FIG. 12C is a graph showing a temporal change in a PA level value before and after a massage measured by an electronic device according to an embodiment of the present disclosure.
Figure 12D:
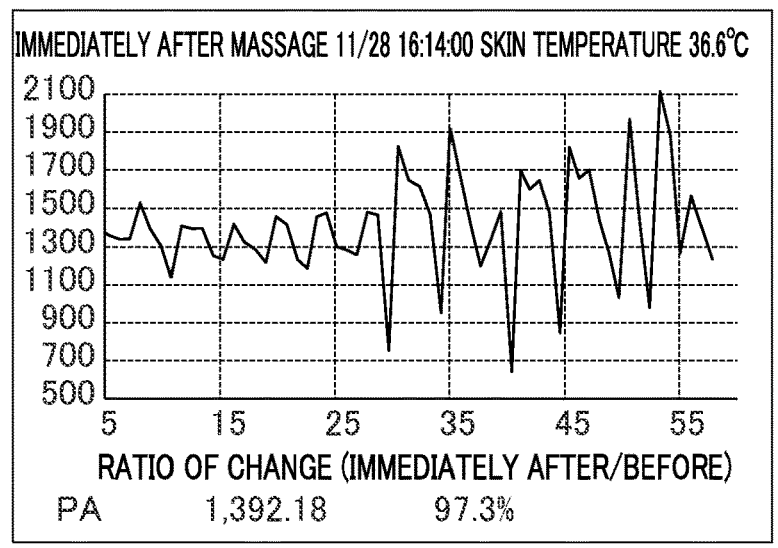
FIG. 12D is a graph showing a temporal change in a PA level value before and after a massage measured by an electronic device according to an embodiment of the present disclosure.
Figure 14A:
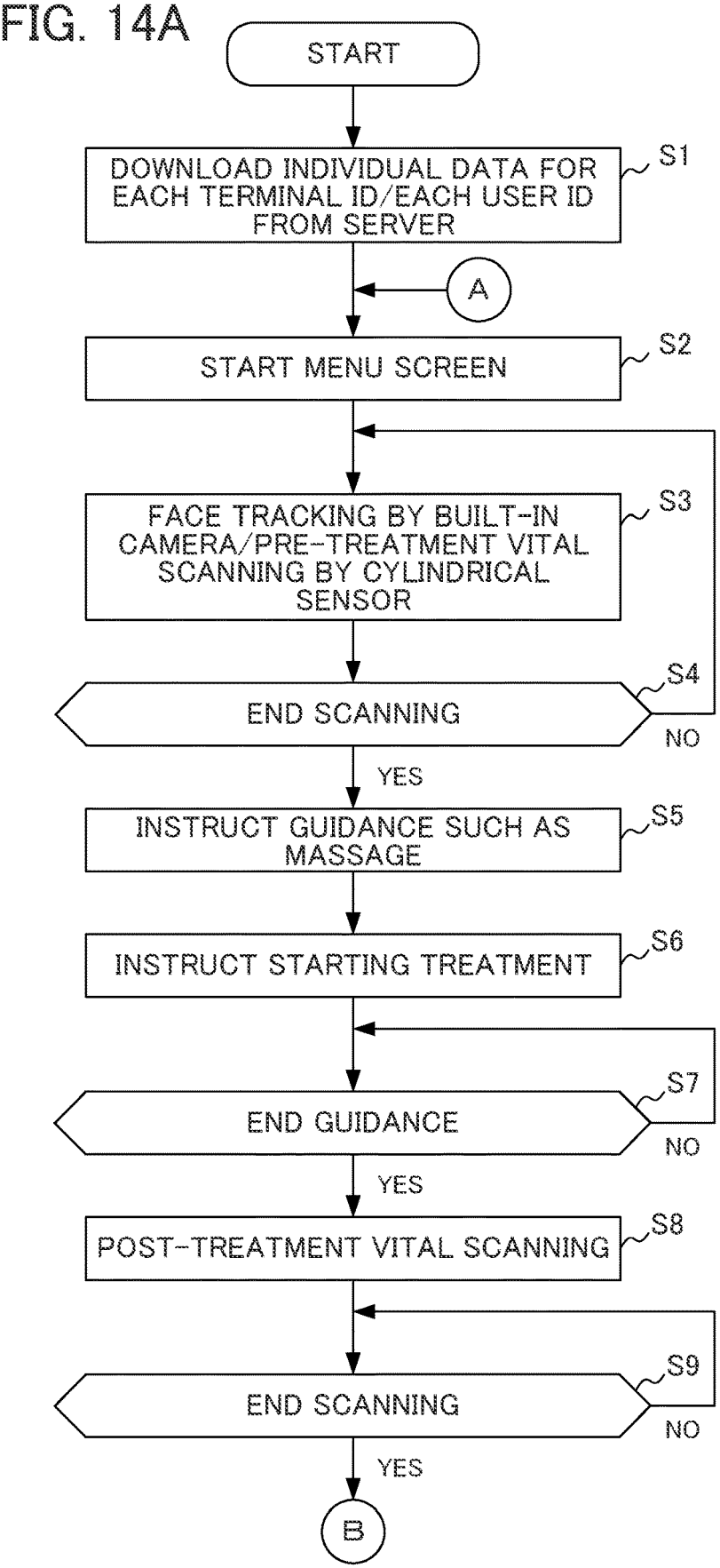
FIG. 14A is a flowchart illustrating a flow of processing executed by an electronic device according to an embodiment of the present disclosure.
Figure 14B:
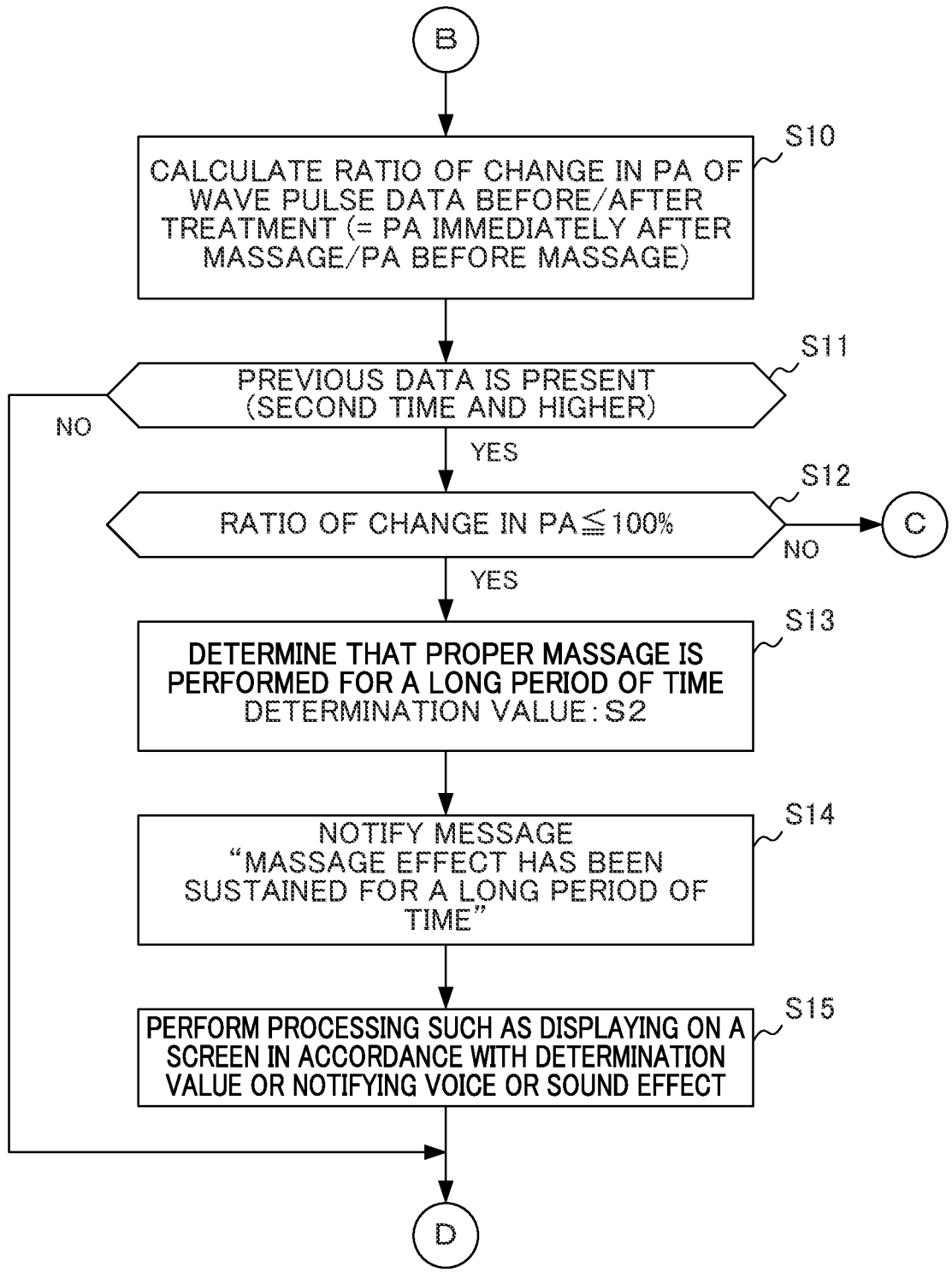
FIG. 14B is a flowchart illustrating a flow of processing executed by an electronic device according to an embodiment of the present disclosure.
Figure 14C:
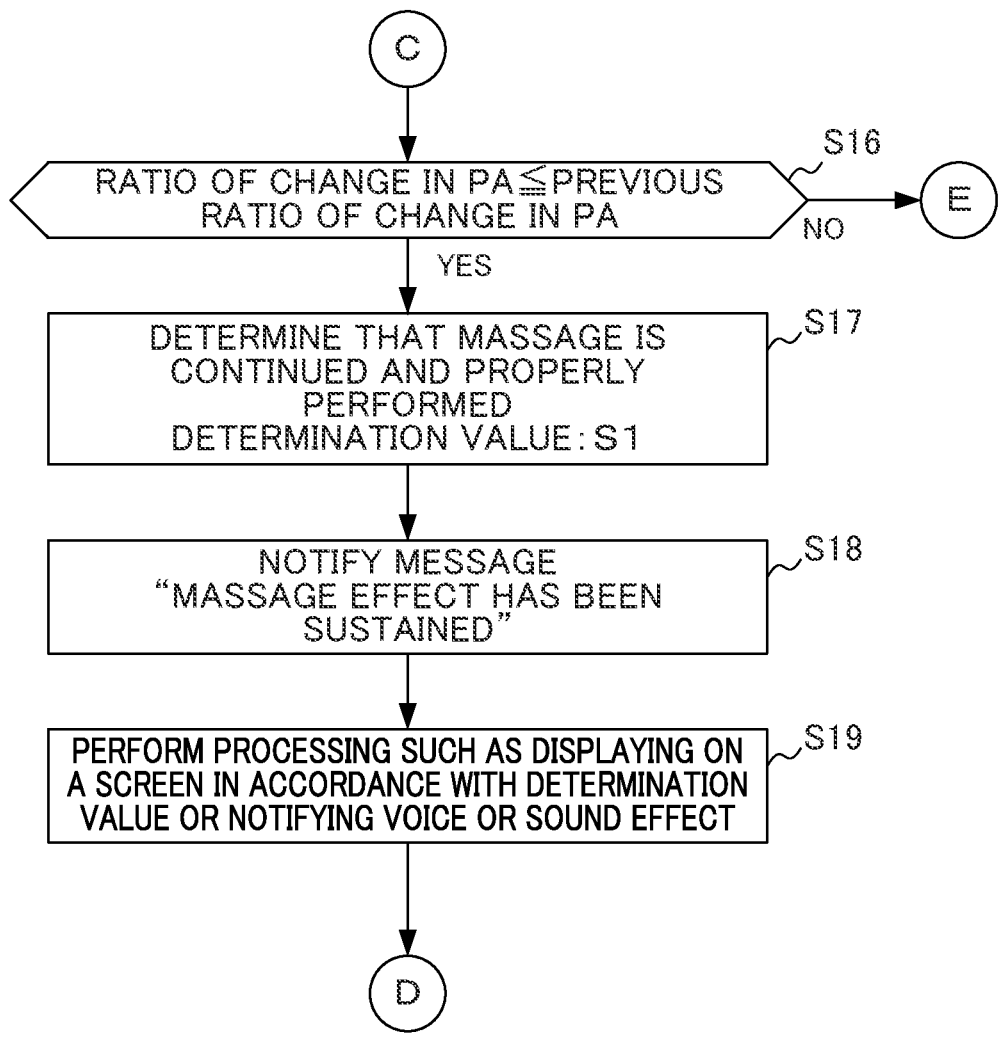
FIG. 14C is a flowchart illustrating a flow of processing executed by an electronic device according to an embodiment of the present disclosure.
Figure 14D:
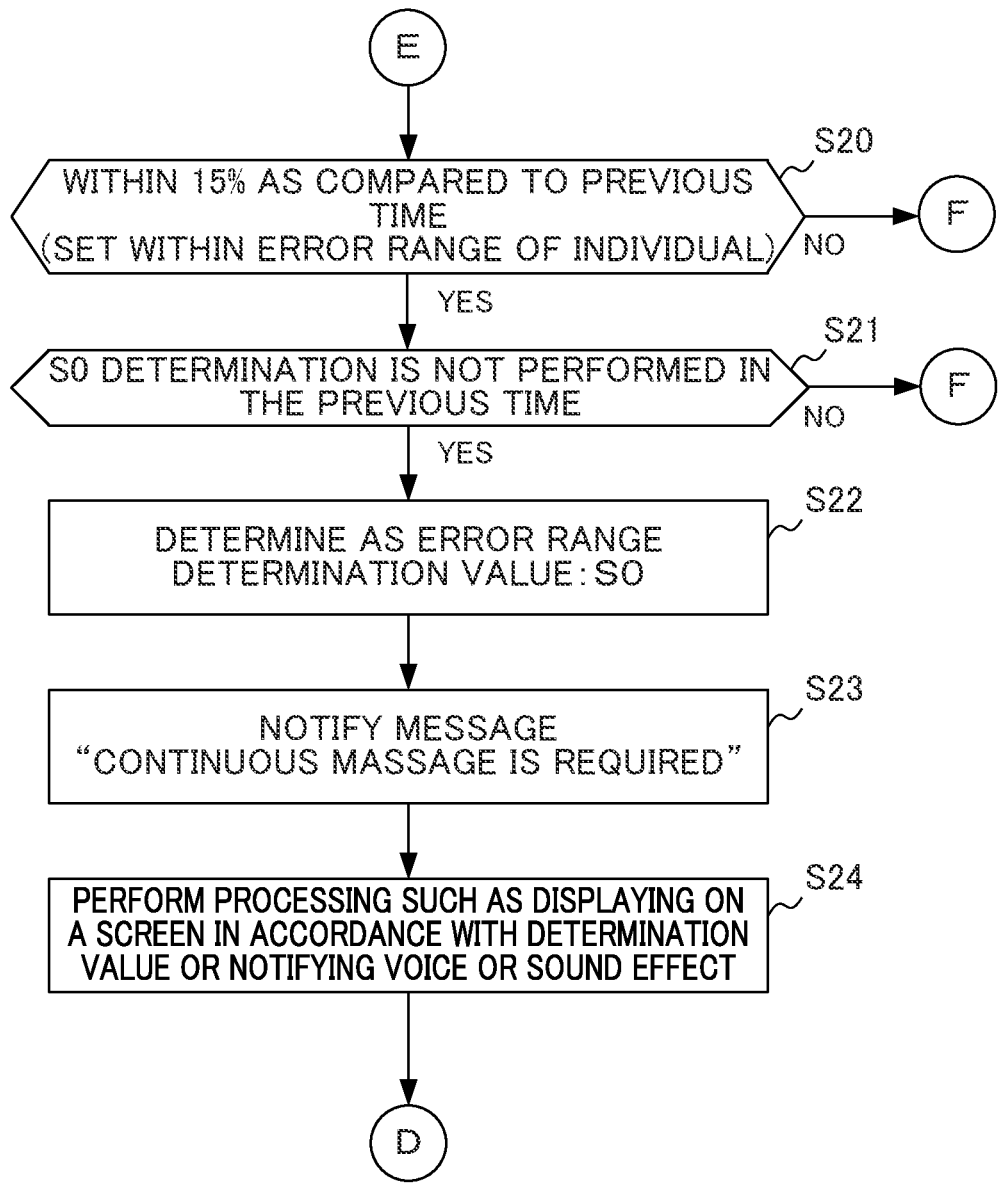
FIG. 14D is a flowchart illustrating a flow of processing executed by an electronic device according to an embodiment of the present disclosure.
Figure 14E:
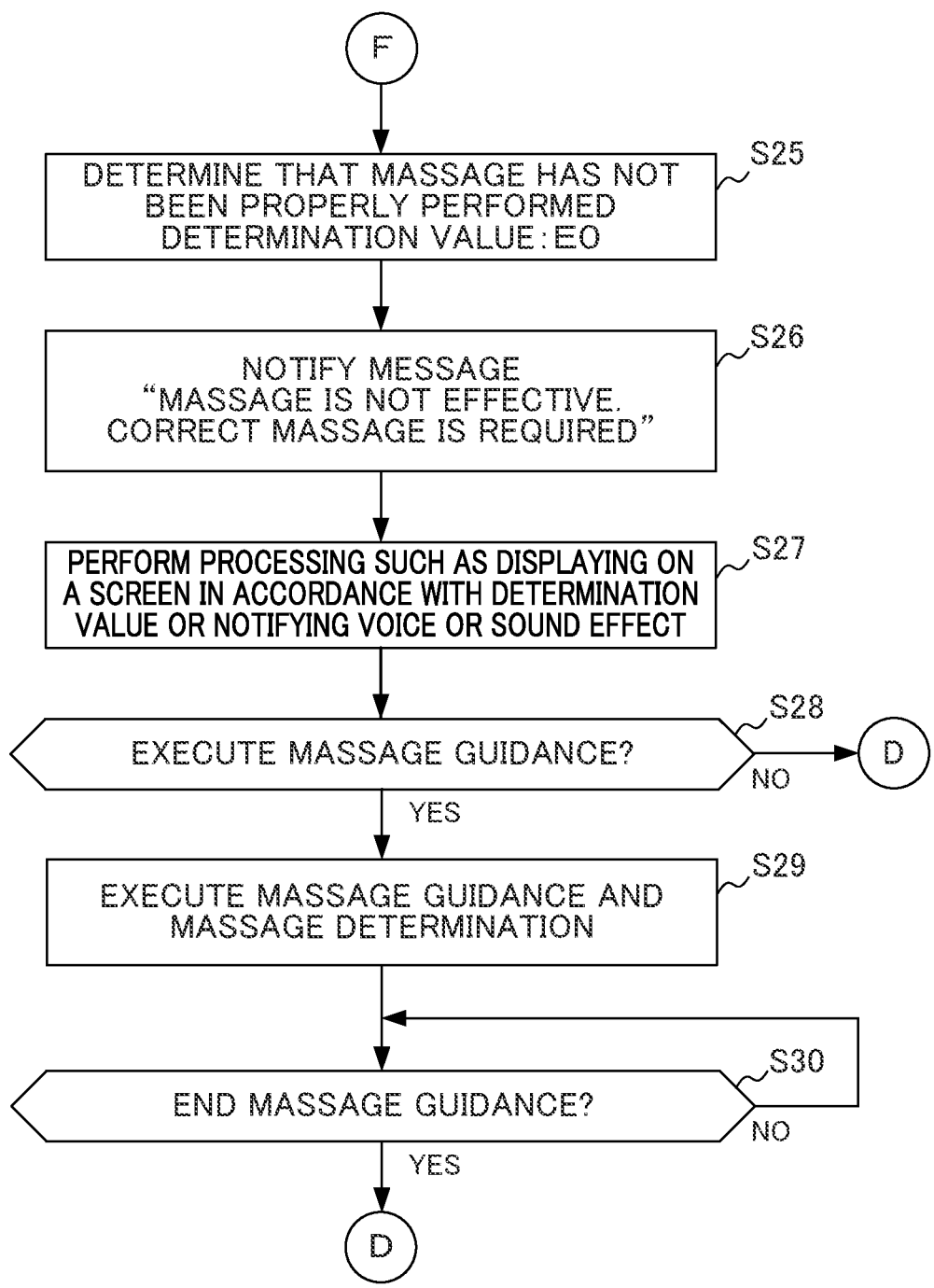
FIG. 14E is a flowchart illustrating a flow of processing executed by an electronic device according to an embodiment of the present disclosure.
Figure 14F:
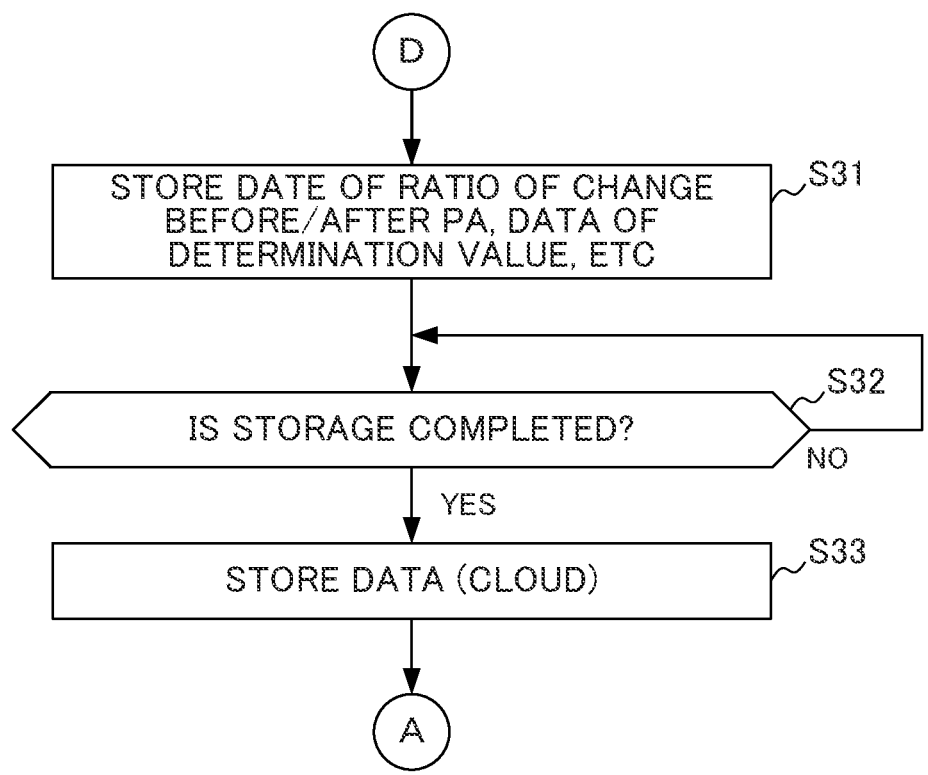
FIG. 14F is a flowchart illustrating a flow of processing executed by an electronic device according to an embodiment of the present disclosure.

8B. Furthermore, FIG. 8D shows a temporal change in the RGB luminance value after massage on November 28, which is the same day.

It should be noted that, since the light that hits the skin is absorbed by the hemoglobin in the blood of the capillaries of the epidermis, the reflected light becomes low. In the present embodiment, since the luminance value is a converted luminance value, the luminance value is lower and the blood flow is larger as the numerical value thereof becomes larger. Furthermore, the RGB luminance value in the graphs reflects the luminance of the RGB signals at a plurality of locations in the measured portion, and is calculated by various methods such as a most frequent value, a median value, and an average value. In the present embodiment, the temporal change in the average value of the luminance of the RGB signals of all the pixels of the measured portion is shown.

Furthermore, FIGS. 9A to 9D each show a graph in which only the luminance value of the G signal is extracted from the temporal change in the RGB illuminance value, and the vertical axis is enlarged. FIGS. 9A, 9B, 9C, and 9D respectively correspond to FIGS. 8A, 8B, 8C, and 8D. It should be noted that the converted luminance in the graphs reflects the luminance of the green signal at a plurality of locations in the region to be measured, and is calculated by various methods such as a most frequent value, a median value, and an average value. In the present embodiment, the temporal change of the average value of the luminance of the G signal of all the pixels of the measured portion is acquired as the representative pulse wave information.

Furthermore, FIGS. 10A to 10D each show a graph in which the temporal change in the R signal shown in FIGS. 8A to 8D is subtracted from the temporal change in the luminance value of the G signal shown in FIGS. 9A to 9D in order to suppress the influence of disturbance. FIGS. 10A, 10B, 10C, and 10D respectively correspond to FIGS. 8A and 9A, 8B and 9B, 8C and 9C, and 8D and 9D.

Incidentally, the pulse wave has an amplitude. FIG. 11 is a diagram schematically showing the amplitude PA (Pulse Amplitude) of the pulse wave measured by the electronic device 1 according to an embodiment of the present disclosure. As shown in FIG. 11, the pulse wave analyzed from the video shows a periodic waveform showing a waveform within a range of a constant amplitude PA. The amplitude PA of this pulse wave indicates the difference between the adjacent maximum and minimum values of the pulse wave signal. It should be noted that the range for acquiring the amplitude PA is preferably a region in which the amplitude is stable without abnormal values. For example, when an abnormal value exceeding a preset threshold value is detected, the pulse wave information is acquired so that the abnormal value is excluded.

Alternatively, it is also possible to display a message that the video could not be appropriately acquired at the time of capturing, and appropriate pulse wave information may be acquired by performing capturing of the video again. Alternatively, the pulse wave after a predetermined period from the start of capturing may be used for the calculation of the amplitude. Alternatively, the amplitude may be calculated by excluding the abnormal value from the pulse wave acquired within a predetermined period of time. As described above, various methods can be applied to the calculation of the amplitude.

FIGS. 12A to 12D each show a temporal change in the PA level value in the first video before and after massage as an event, and a temporal change in the PA level value in the second image before and after massage. More specifically, FIGS. 12A, 12B, 12C, and 12D respectively correspond to FIGS. 10A, 10B, 10C, and 10D.

As is evident from FIGS. 8 to 10 and 12, when viewed from the data on October 3 when the massage was started, there is no change in the luminance values before and after massage in the G luminance value and the G-R value. More specifically, in the G luminance value, the ratio of change in the value after massage compared to the value before massage is 100.2%. Furthermore, regarding the G-R value, the ratio of change in the value after massage compared with the value before massage is 95.8%. On the other hand, comparing the PA level values reveals that the amplitude is greatly increased. More specifically, the ratio of change in the value after massage compared to the value before massage is 136.2%. Furthermore, when viewed from the data on November 28, which is about two months after the massage was started, in the G luminance value and the G-R value, there is no change before and after the massage, and there is no change in the PA level value even when compared therebetween. More specifically, regarding the G luminance value, the ratio of change in the value after massage compared to the value before massage is 97.9%. Furthermore, regarding the G-R value, the ratio of change in the value after massage compared to the value before massage is 96.2%. Furthermore, regarding the PA level value, the ratio of change in the value after massage compared to the value before massage is 97.3%.

FIG. 13 is a graph showing the transitions of the ratio of change of actual measurement values obtained by measuring the PA level values and the offset values of the baseline when a massage over a long period of time has been performed, by the measurement-dedicated camera 25.

As described above, at the beginning of the massage, the PA level value after the massage greatly increases in amplitude as compared with the PA level value before the massage, while the ratio of change in the PA level value after the massage decreases as compared with the PA level value before the massage as the days elapse since the beginning of the massage. Thus, as shown in FIG. 13, by observing the change in the PA level value, the effect of the treatment such as massage over a long period of time is found, and when the massage is properly performed, it is exhibited that the dilation of the capillaries of the skin continues.

More specifically, when massage is performed over a long period of time in the treatment, the ratio of change in the PA level value based on video pulse wave before and after the treatment is gradually decreased. This is because the capillaries are expanded by external pressure due to massage and continue to expand, so that the expansion is maintained and the ratio of change is reduced. The electronic device 1 determines whether or not the massage is properly performed, based on the ratio of change (decreased value), and determines whether or not the optimal massage is continued. In addition, the electronic device 1 notifies the user of whether or not an appropriate massage has been performed by performing an appropriate notification or guidance instruction in accordance with these values. If there is no decrease in the PA level value, the electronic device 1 notifies that an appropriate massage has not been performed, and instructs an appropriate massage.

Therefore, by determining the effect based on the transition shown in FIG. 13 and appropriately notifying the user of the effect, the user can perform the treatment while actually feeling the effect while maintaining the motivation necessary for self-care, so that the treatment can be continuously performed over a long period of time and skin turnover can be performed without stagnation.

It should be noted that, in order to improve the determination accuracy, by simultaneously recording the time and the number of times since the start of the treatment, the determination accuracy can be improved by changing the ratio of change as a reference to 1 month (120% or more as an example), 2 months (110% or more as an example), and 3 months or later (90% or more as an example).

In addition, the degree of effect may be changed according to age. For example, there is a method in which the standard range of the ratio of change may be 90% to 140% in the case of a person in his/her 20s, while the standard range of change may be 90% to 110% in the case of a person aged 60 or older.

It is also conceivable to change the determination according to the difference between men and women with the above-mentioned age. In the case of males, the ratio of change may be reduced by 10%, and in the case of females, the ratio of change may be increased by 10%.

In addition, it is also possible to set the acceptance criterion according to the skin quality by combining with the function of examining the skin quality in advance. For example, if the skin quality is younger (the skin age is younger), it may be increased by 10% relative to the reference range (e.g., 90% to 130%), and if the skin quality is aged (the skin age is older), it may be decreased by 10% relative to the reference range.

In addition, by accumulating data in the cloud, it is conceivable to generate a discriminator by performing machine learning by clustering processing of classifying data into a set of similar ones based on data stored with tags of actual age and gender, and to create a criterion for determination.

Next, the flow of processing of analyzing the video will be described by referring to FIGS. 14A to 14F. FIGS. 14A to 14F are flowcharts illustrating the flow of processing performed by the electronic device 1 of FIG. 1 having the functional configuration of FIG. 7.

As shown in FIG. 14A to FIG. 14F, in step S1, the information processing unit 115 downloads personal data from the server group 3 for each terminal ID of the electronic device 1 and each user ID of the user of the electronic device 1.

In step S2, the display processing unit 112 starts the menu screen.

In step S3, the video processing unit 111 performs face tracking using the imaging unit 16, which is a built-in camera, and performs pretreatment vital scanning using the measurement-dedicated camera 25, which is a cylindrical sensor.

In step S4, when the scanning is completed (S4: YES), the processing advances to step S5. On the other hand, if the scanning has not been completed yet (S4: NO), the processing advances to step S4.

In step S5, the video processing unit 111 instructs the display processing unit 112 to display the guidance of an operation such as a massage.

In step S6, the display processing unit 112 performs a display for instructing the user to start the treatment.

In step S7, if the treatment guidance is completed (S7: YES), the processing advances to step S8. If the treatment guidance has not been completed yet (S7: NO), the processing advances to step S7.

In step S8, the video processing unit 111 performs a post-treatment vital scan using the measurement-dedicated camera 25 which is a cylindrical sensor.

In step S9, when the post-treatment vital scan is completed (S9: YES), the processing advances to step S10. If the post-treatment vital scan has not been completed yet (S9: NO), the processing advances to step S9.

In step S10, the result processing unit 113 calculates the ratio of change in the PA level before and after the treatment, i.e. the ratio of the PA level value immediately after the massage to the PA level value before the massage.

In step S11, in a case in which there is the data of the ratio of change in the previous PA level value (S11: YES), the processing advances to step S12. In a case in which there is no data of the ratio of change in the previous PA level value due to this time being the first massage or the like (S11: NO), the processing advances to step S31.

In step S12, in a case in which the ratio of change in the PA level value before and after massage is 100% or less (S12: YES), the processing advances to step S13. In a case in which the ratio of change in the PA level value before and after the massage exceeds 100% (S12: NO), the processing advances to step S16.

In step S13, the evaluation processing unit 114 determines that the massage has been properly performed over a long period of time. Furthermore, the difference between the ratio of change in the PA level value before and after the massage used in step S12 and 100% is set as a determination value S2.

In step S14, the display processing unit 112 notifies a message saying that "the massage effect has been sustained over a long period of time".

In step S15, the display processing unit 112 performs processing such as displaying on a screen in accordance with the determination value S2 or notifying a voice or sound effect. Thereafter, the processing advances to step S31.

In step S16, in a case in which the ratio of change in the PA level value before and after the massage is equal to or less than the previous ratio of change (S16: YES), the processing advances to step S17. In a case in which the ratio of change in the PA level value before and after the massage exceeds the previous ratio of change (S16: NO), the processing advances to step S20.

In step S17, the evaluation processing unit 114 determines that the massage has been continued and properly performed. Furthermore, the difference between the ratio of change in the PA level value before and after the massage used in step S16 and the previous ratio of change is set as the determination value S1.

In step S18, the display processing unit 112 notifies a message that the massage effect is maintained.

In step S19, the display processing unit 112 performs processing such as displaying on a screen in accordance with the determination value S1 or notifying a voice or sound effect. Thereafter, the processing advances to step S31.

In step S20, in a case in which the degree of the ratio of change in the PA level value before and after the massage having exceeded the previous ratio of change falls within 15% (S20: YES), the processing advances to step S21. In a case in which the degree of the ratio of change in the PA level value before and after the massage having exceeded the previous ratio of change exceeds 15% (S20: NO), the processing advances to step S25. It should be noted that the above 15% refers to an error range in which a different value is set for each individual person.

In step S21, in a case in which "S0 determination" is not performed at the time of the previous processing, that is, in a case in which a value is not substituted for a determination value S0 described later (S21: YES), the processing advances to step S22. In a case in which "S0 determination" is performed at the time of the previous processing, that is, in a case in which a value has been substituted for the determination value S0 described later (S21: NO), the processing advances to step S25.

In step S22, the evaluation processing unit 114 determines the ratio of change in the PA level value before and after the massage as an error range. Furthermore, the evaluation processing unit 114 determines the difference between the ratio of change in the PA level value before and after the massage used in step S16 and 15% as the determination value S0.

In step S23, the display processing unit 112 notifies a message saying "Continue massage".

In step S24, the display processing unit 112 performs processing such as displaying on a screen in accordance with the determination value S0, or notifying a sound or sound effect. Thereafter, the processing advances to step S31.

In step S25, the evaluation processing unit 114 determines that the massage is not performed properly. Furthermore, the evaluation processing unit 114 determines the difference between the ratio of change in the PA level value before and after the massage used in step S16 and 15% as a determination value E0.

In step S26, the display processing unit 112 notifies a message saying "Massage is not effective. Proper massage is required".

In step S27, the display processing unit 112 performs processing such as displaying on a screen in accordance with the determination value E0, notifying a sound or sound effect.

In step S28, in a case in which the massage guidance is executed (S28: YES), the processing advances to step S29. In a case in which the massage guidance is not executed (S28: NO), the processing advances to step S31.

In step S29, the display processing unit 112 executes the massage guidance and a massage determination. Here, as the "massage determination", for example, whether or not the massage has been effectively performed may be determined by performing the image processing using the coordinate value of the eyes, the nose, or the mouth by face recognition on an image such as a face captured by the imaging unit 16 or the measurement-dedicated camera 25.

In step S30, in a case in which the massage guidance is terminated (S30: YES), the processing advances to step S31. In a case in which the massage guidance is not terminated (S30; NO), the processing advances to step S30.

In step S31, the information processing unit 115 stores the ratio of change in the PA level value before and after the massage in the server group 3 with a date added to data such as the determination value.

In step S32, in a case in which the storage of the data in the server group 3 is completed (S32: YES), the processing advances to step S33. In a case in which the storage of the data in the server group 3 has not been completed (S32: NO), the processing advances to step S32.

In step S33, the information processing unit 115 stores the above-described data in the cloud. Thereafter, the processing advances to step S2.

A description will be given of the effects derived from the electronic device 1 according to the present embodiment.

The electronic device 1 according to the present embodiment includes the video processing unit 111, the result comparison unit 113, and the evaluation processing unit 114. The video processing unit 111 acquires, based on video information of a body in a first video obtained by image-capturing at least a portion of the body, first pulse wave amplitude information indicating an amplitude of a pulse wave of the body within a predetermined period of time, and acquires, based on video information of the body in a second video obtained by image-capturing at least a portion of the body after image-capturing the first video, second pulse wave amplitude information indicating an amplitude of a pulse wave of the body within a predetermined period of time. The result processing unit 113 compares the first pulse wave amplitude information with the second pulse wave amplitude information to output a comparison result indicating a degree of variation in a blood flow. The storage unit 19 stores the comparison result outputted from the result processing unit 113. The evaluation processing unit 114 acquires a trend in variation of the blood flow based on a comparison result newly outputted by the result processing unit 113 and the comparison result previously stored in the memory.

With such a configuration, it is possible to precisely measure an effect from a continuously performed cosmetic treatment, etc. In particular, in skincare, etc., the PA (pulse wave amplitude) gradually decreases after treatment such as massage over a long period of time. By the user performing a continuous treatment while the electronic device 1 notifying and advising the user of the electronic device 1 of whether an effective treatment has been performed based on this ratio of change, skin turnover can be performed without stagnation, making it possible to perform an effective treatment.

Furthermore, the second video is acquired after an event performed by a user after image-capturing the first video, and the evaluation processing unit 114 evaluates whether or not the event is continuously performed based on a trend in variation of a blood flow.

With such a configuration, the electronic device 1 determines whether a treatment such as massage has been performed continuously over a long period of time, and it becomes possible to urge the user to continue a treatment over a long period of time by notifying the user of the electronic device 1 with a message based on the determination.

In a case in which a pulse wave amplitude of the second pulse wave amplitude information is equal to or less than a pulse wave amplitude of the first pulse wave amplitude information in a state in which one or more of the comparison results is stored in the storage unit 19, the evaluation processing unit 114 evaluates that the event is continuously performed.

With such a configuration, when using the ratio of change in the PA level value as a pulse wave amplitude, in a case in which a treatment such as massage has been properly performed, it becomes possible for the user to sufficiently know the effect from treatment such as massage over a long period of time based on the fact that the dilation of the capillaries of the skin continues.

Furthermore, in a case in which a ratio of the comparison result newly outputted by the result processing unit 113 to the comparison result previously stored in the storage unit 19 falls within a predetermined range, the evaluation processing unit 114 evaluates that the event is continuously performed.

With such a configuration, by eliminating specific data such as noise, it becomes possible to determine whether massage has continued appropriately based on the effect of the massage more precisely.

Furthermore, in a case in which the result processing unit 113 outputs a comparison result that is newly determined, the evaluation processing unit 114 further acquires a trend in variation of a blood flow based on a plurality of the comparison results which are previous and a current comparison result.

With such a configuration, the influence from the error included in the variation in the blood flow acquired based on the previous one-time comparison result, it becomes possible to understand the degree of variation in the blood flow much more precisely.

Modifications

The present disclosure is not limited to the above-described embodiments, and modifications, improvements, and the like within the scope that can achieves the object of the present disclosure are included in the present disclosure. For example, the embodiments described above may be modified as the following modifications.

In the above embodiment, a configuration has been described in which the comparison processing using the converted luminance value subjected to processing of converting with respect to the detected luminance; however, the present disclosure is not limited to this configuration. The converted luminance value is one mode indicating the level of luminance, and thus, the conversion processing may be omitted from the above embodiment, and the processing may be performed using the detected luminance value without performing the conversion processing.

It is possible to incorporate a mirror unit having a reflecting surface into the display unit 18 of the electronic device 1 of the above embodiment. In this case, the mirror unit is realized by a half mirror having both transmission characteristics and reflection characteristics, as an optical characteristic. The mirror unit is disposed to be superimposed on the front surface of the display unit 18 in a direction in which the user visually recognizes the mirror unit. With such a configuration, for example, the user can visually recognize not the user image captured by the imaging unit 16, but rather the face of the user, which is reflected by the mirror unit, and various kinds of information (for example, a composite image) displayed on the display unit 18 and transmitted through the mirror unit at the same time. That is, in the above-described embodiment above, the user image captured by the imaging unit 16 as a subject is visually recognized as a real image of the user; however, in the present modification example, a mirror image of the user reflected by the mirror unit is visually recognized as the real image of the user. Even in this way, it is possible to provide the same effect as in the above-described embodiment.

OTHER MODIFIED EXAMPLES

For example, in the above embodiment, it is assumed that the electronic device 1 cooperates with the respective servers included in the server group 3, but the functions of the respective servers may be added to the electronic device 1, and all the processes may be performed only in the electronic device 1.

In addition, in the above embodiment, the electronic device 1 to which the present invention is applied has been described by way of example of an electronic device incorporated in a portable self-standing mirror, but the present invention is not particularly limited thereto. For example, the present invention can be applied to an electronic device incorporated into a large mirror such as a full-length mirror, an electronic device incorporated into a stationary bathroom vanity, and a mirror-shaped electronic device installed in a bathroom.

The processing sequence described above can be executed by hardware, and can also be executed by software. In other words, the functional configuration of FIG. 7 is merely an illustrative example, and the present invention is not particularly limited thereto. More specifically, the types of functional blocks employed to realize the above-described functions are not particularly limited to the examples shown in FIG. 7, so long as the electronic device 1 can be provided with the functions enabling the aforementioned processing sequence to be executed in its entirety.

In addition, a single functional block may be configured by a single piece of hardware, a single installation of software, or a combination thereof. The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated Circuit) or FPGA (Field-Programmable Gate Array).

In the case of having the series of processing executed by software, the program constituting this software is installed from a network or recording medium to a computer or the like. The computer may be a computer equipped with dedicated hardware. In addition, the computer may be a computer capable of executing various functions, e.g., a general purpose personal computer, by installing various programs.

The storage medium containing such a program can not only be constituted by the removable medium 100 of FIG. 5 distributed separately from the device main body for supplying the program to a user, but also can be constituted by a storage medium or the like supplied to the user in a state incorporated in the device main body in advance. The removable medium 100 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 12 of FIG. 4 in which the program is recorded or a hard disk included in the storage unit 19 of FIG. 4 or 5, etc.

It should be noted that, in the present specification, the steps defining the program recorded in the storage medium include not only the processing executed in a time series following this order, but also processing executed in parallel or individually, which is not necessarily executed in a time series. Further, in the present specification, the terminology of the system means an entire apparatus including a plurality of apparatuses and a plurality of units.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:

1. An electronic device comprising:
a memory; and at least one processor,
wherein the at least one processor executes a program stored in the memory to perform operations comprising:
(a) acquiring a first video of a body of a user, the first video being obtained by image-capturing at least a portion of the body,
(b) acquiring, based on video information of the first video of the body, first pulse wave amplitude information indicating an amplitude of a pulse wave indicative of a blood flow of the body within a predetermined period of time,
(c) acquiring a second video of the body, the second video being obtained by image-capturing at least said portion of the body at a timing after a timing at which the first video was image-captured,
(d) acquiring, based on video information of the second video of the body, second pulse wave amplitude information indicating an amplitude of a pulse wave indicative of the blood flow of the body within a predetermined period of time,
(e) comparing the first pulse wave amplitude information with the second pulse wave amplitude information, and outputting a comparison result indicating a degree of variation in the blood flow of the body,
(f) storing the outputted comparison result in the memory, and
(g) after having performed said operations (a)-(f) at least one time to obtain at least one previous comparison result which is stored in the memory and subsequently performing said operations (a)-(e) an additional time to thereby obtain a new comparison result which is more recently outputted by the at least one processor than the at least one previous comparison result, acquiring a trend in variation of the blood flow of the body between each respective set of the first pulse wave amplitude information and the second pulse wave amplitude information acquired each time operations (a)-(e) are performed, based on the new comparison result and the at least one previous comparison result,
wherein:
a new first video and a new second video are used each time said operations (a)-(e) are performed,
the second video is image-captured after an event is performed by the user at a timing after the timing at which the first video was image-captured, the event being an event performed on an area of the body to increase the blood flow of the body in the area on which the event is performed,
the at least one processor evaluates whether the event has been performed at least twice over a certain period of time, based on a detection at a time of obtaining the new comparison result that the at least one previous comparison result is stored in the memory, and
in response to evaluating that the event has been performed at least twice over the certain period of time, the at least one processor evaluates an effectiveness of the event performed at least twice by the user over the certain period of time based on the trend in variation of the blood flow of the body over the at least two times that the event has been performed.

2. The electronic device according to claim 1, wherein, in a case in which the pulse wave amplitude of the second pulse wave amplitude information is equal to or less than the pulse wave amplitude of the first pulse wave amplitude information in a state in which one or more of the comparison results is stored in the memory, the at least one processor evaluates that the event performed by the user has been effective.

3. The electronic device according to claim 1, wherein, in a case in which a ratio of the new comparison result to the at least one previous comparison result falls within a predetermined range, the at least one processor evaluates that the event performed by the user has been effective.

4. The electronic device according to claim 1, wherein, in a case in which the at least one previous comparison result stored in the memory includes at least two previous comparison results, the at least one processor further acquires the trend in variation of the blood flow of the body based on the new comparison result, which is more recently outputted by the at least one processor than the at least two previous comparison results, and the at least two previous comparison results.

5. A control method for an electronic device executed by a computer including at least one processor, the control method causing the at least one processor to execute a program stored in a memory to perform operations comprising:
(a) acquiring a first video of a body of a user, the first video being obtained by image-capturing at least a portion of the body,
(b) acquiring, based on video information of the first video of the body, first pulse wave amplitude information indicating an amplitude of a pulse wave indicative of a blood flow of the body within a predetermined period of time,
(c) acquiring a second video of the body, the second video being obtained by image-capturing at least said portion of the body at a timing after a timing at which the first video was image-captured,
(d) acquiring, based on video information of the second video of the body, second pulse wave amplitude information indicating an amplitude of a pulse wave indicative of the blood flow of the body within a predetermined period of time,
(e) comparing the first pulse wave amplitude information with the second pulse wave amplitude information, and outputting a comparison result indicating a degree of variation in the blood flow of the body,
(f) storing the outputted comparison result in the memory, and
(g) after having performed said operations (a)-(f) at least one time to obtain at least one previous comparison result which is stored in the memory and subsequently performing said operations (a)-(e) an additional time to thereby obtain a new comparison result which is more recently outputted by the at least one processor than the at least one previous comparison result, acquiring a trend in variation of the blood flow of the body between each respective set of the first pulse wave amplitude information and the second pulse wave amplitude information acquired each time operations (a)-(e) are performed, based on the new comparison result and the at least one previous comparison result,
wherein a new first video and a new second video are used each time said operations (a)-(e) are performed,
wherein the second video is image-captured after an event is performed by the user at a timing after the timing at which the first video was image-captured, the event being an event performed on an area of the body to increase the blood flow of the body in the area on which the event is performed, and
wherein the operations further comprise:

evaluating whether the event has been performed at least twice over a certain period of time, based on a detection at a time of obtaining the new comparison result that the at least one previous comparison result is stored in the memory, and in response to evaluating that the event has been performed at least twice over the certain period of time, evaluating an effectiveness of the event performed at least twice by the user over the certain period of time based on the trend in variation of the blood flow of the body over the at least two times that the event has been performed.

6. The control method according to claim 5, wherein the evaluating the effectiveness comprises evaluating that the event performed by the user has been effective in a case in which the pulse wave amplitude of the second pulse wave amplitude information is equal to or less than the pulse wave amplitude of the first pulse wave amplitude information in a state in which one or more of the comparison results is stored in the memory.

7. The control method according to claim 5, wherein the evaluating the effectiveness comprises evaluating that the event performed by the user has been effective in a case in which a ratio of the new comparison result to the at least one previous comparison result falls within a predetermined range.

8. The control method according to claim 5, wherein, in a case in which the at least one previous comparison result stored in the memory includes at least two previous comparison results, the operations further comprise acquiring the trend in variation of the blood flow of the body based on the new comparison result, which is more recently outputted than the at least two previous comparison results, and the at least two previous comparison results.

9. A non-transitory computer-readable storage medium storing a program that is executed by a computer that comprises at least one processor to control an electronic device, the program being executable to cause the computer to perform operations comprising:

(a) acquiring a first video of a body of a user, the first video being obtained by image-capturing at least a portion of the body, (b) acquiring, based on video information of the first video of the body, first pulse wave amplitude information indicating an amplitude of a pulse wave indicative of a blood flow of the body within a predetermined period of time, (c) acquiring a second video of the body, the second video being obtained by image-capturing at least said portion of the body at a timing after a timing at which the first video was image-captured, (d) acquiring, based on video information of the second video of the body, second pulse wave amplitude information indicating an amplitude of a pulse wave indicative of the blood flow of the body within a predetermined period of time, (e) comparing the first pulse wave amplitude information with the second pulse wave amplitude information, and outputting a comparison result indicating a degree of variation in the blood flow of the body, (f) storing, by a storing function, the outputted comparison result, and (g) after having performed said operations (a)-(f) at least one time to obtain at least one previous comparison result which is stored by the storing function and subsequently performing said operations (a)-(e) an additional time to thereby obtain a new comparison result which is more recently outputted by the at least one processor than the at least one previous comparison result, acquiring a trend in variation of the blood flow of the body between each respective set of the first pulse wave amplitude information and the second pulse wave amplitude information acquired each time operations (a)-(e) are performed, based on the new comparison result and the at least one previous comparison result, wherein a new first video and a new second video are used each time said operations (a)-(e) are performed, wherein the second video is image-captured after an event is performed by the user at a timing after the timing at which the first video was image-captured, the event being an event performed on an area of the body to increase the blood flow of the body in the area on which the event is performed, and wherein the operations further comprise:

evaluating whether the event has been performed at least twice over a certain period of time, based on a detection at a time of obtaining the new comparison result that the at least one previous comparison result is stored in the memory, and in response to evaluating that the event has been performed at least twice over the certain period of time, evaluating an effectiveness of the event performed at least twice by the user over the certain period of time based on the trend in variation of the blood flow of the body over the at least two times that the event has been performed.

* * * * *